US006797513B2

(12) United States Patent
Ullrich et al.

(10) Patent No.: US 6,797,513 B2
(45) Date of Patent: Sep. 28, 2004

(54) NUCLEIC ACID ENCODING CLK2 PROTEIN KINASES

(75) Inventors: Axel Ullrich, München (DE); Oliver Nayler, Graefehing (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 53 days.

(21) Appl. No.: 09/905,999

(22) Filed: Jul. 17, 2001

(65) Prior Publication Data

US 2002/0106771 A1 Aug. 8, 2002

Related U.S. Application Data

(63) Continuation of application No. 09/127,248, filed on Jul. 31, 1998, now abandoned, which is a continuation-in-part of application No. 08/877,150, filed on Jun. 17, 1997.
(60) Provisional application No. 60/034,286, filed on Dec. 19, 1996.

(51) Int. Cl.$^7$ .............................. C12N 9/12; C12N 15/11
(52) U.S. Cl. ...................... 435/325; 435/69.1; 435/194; 435/320.1; 435/252.3; 435/254.11; 536/23.1; 536/23.5; 530/300; 530/350
(58) Field of Search ................................. 530/300, 350; 536/23.1, 23.5; 435/69.1, 320.1, 325, 252.3, 254.11, 194; 424/94.1

(56) References Cited

U.S. PATENT DOCUMENTS

| | | |
|---|---|---|
| 4,945,050 A | 7/1990 | Samford et al. |
| 5,283,173 A | 2/1994 | Fields et al. |

FOREIGN PATENT DOCUMENTS

| | | |
|---|---|---|
| WO | WO 93/09236 | 5/1993 |
| WO | WO 94/23039 | 10/1994 |
| WO | WO 96/18738 | 6/1996 |
| WO | WO 97/35019 A | 9/1997 |
| WO | WO 97/48723 | 12/1997 |

OTHER PUBLICATIONS

GenBank Database Accession No. W89331 (version GI:1538524), Sep. 12, 1996, accessed Jan. 22, 2001.
GenBank Database Accession No. AA059682 (verison GI: 1553435), Sep. 23, 1996, accessed Jan. 22, 2001.
Nayler et al., "Characterization and comparison of four serine– and arginine–rich (SR) protein kinases," *Biochem. J.*, 326:693–700 (1997).
Yang et al., "Cloning and Expression of PTP–PEST a Novel, Human, Nontranmembrane Protein Tyrosine Phosphatase," *J. Biol. Chem.* 268(9):6622–6628 (1993).
Tomic et al., "Association of SH2 Domain Protein Tyrosine Phosphatases with the Epidermal Growth Factor Receptor in Human Tumor Cells: Phosphatidic Acid Activites Receptor Dephosphorylation by PTP1C," *J. Biol. Chem.* 270:21277–21284 (1995).

Saito and Streuli, "Molecular Characterization of Protein Tyrosine Phosphatases," *Cell Growth & Differentation* 2(1):59–65 (1991).
Ben–David et al., "A Mammalian Protein Kinase With Potential For Serine/Threonine and Tyrosine Phosphorylation is Related to Cell Cycle Regulators," *EMBO Journal* 10(2):317–325 (1991).
Aoki et al., "The Novel Protein–Tyrosine Phosphatase PTP20 Is a Positive Regulator of PC12 Cell Neuronal Differentiation," *J. Biol. Chem.* 271(46):29422–29426 (1996).
Cheng et al., "A Novel Protein Tyrosine Phosphatase Expressed in lin$^{lo}$CD34$^{hi}$Sca$^{hi}$ Hematopoietic Progenitor Cells," *Blood* 88:1156–1167 (1996).
EMBL Accession No. U49853, "Sequence Mus Musculus Protein Tyrosine Phosphatase nRNA, Complete cds", XP–002034266 (Mar. 27, 1996).
EMBL Accession No. U55057, "Mus Musculus Receptor Protein Tyrosine Phosphatase–Lamda (Ptp–Lambda) Mrna, Complete cds.," XP–002064044.
Wang et al., "Characterization of PCP–2, a Novel Receptor Protein Tyrosine Phosphatase of the MAM Domain Family," *Oncogene* 12(12):2555–2562 (1996).
Kim et al, "Characterization of the PEST family protein tyrosine phosphatase BDP1," *Oncogene* 13(10):2275–2279 (1996).
Winfield et al., "Identification of Three Additional Genes Contiguous to the Glucocerebrosidase Locus on Chromosome 1q21: Implications for Gaucher Disease," *Genome Research* 7(10):1020–1026 (1997).
Hanes et al., "Characterization by cDNA Cloning of Two New Human Protein Kinases: Evidence by Sequence Comparison of a New Family of Mammalian Protein Kinases," *J. Mol. Biol.* 244(5):665–672 (1994).

(List continued on next page.)

Primary Examiner—Lorraine Spector
Assistant Examiner—Claire M. Kaufman
(74) Attorney, Agent, or Firm—Beth A. Burrous; Foley & Lardner

(57) ABSTRACT

The present invention relates to nucleic acid molecules encoding mCLK2, mCLK3, and mCLK4 polypeptides, nucleic acid molecules-encoding portions of their amino acid sequences, nucleic acid vectors harboring such nucleic acid molecules, cells containing such nucleic acid vectors, purified polypeptides encoded by such nucleic acid molecules, and antibodies to such polypeptides. Also included are assays that contain at least one CLK protein kinase related molecule. Diagnosis and treatment of an abnormal condition related to RNA splicing or cell proliferation in an organism by using a CLK protein kinase related molecule or compound are disclosed. A method of using a CLK protein kinase related molecule or compound as a contraceptive to reproduction in male organisms is also disclosed.

8 Claims, 7 Drawing Sheets

OTHER PUBLICATIONS

Becker et al., "cDNA cloning and characterization of rat Clk3, a LAMMER kinase predominatly expressed in tests," *Biochim. Biophy. Acta* 1312(1):63–67 (1996).

Wu et al., "Molecular Cloning of a Transcriptional Repressor Protein (SIRP–1) Which Binds to the Intestine–Specific Promoter Region of the Sucrase–Isomaltase Gene," *Gastroenterolgy* 104(4, part 2):A290 abstract (1993).

Johnson and Smith, "Molecular Cloning of a Novel Human cdc2/CDC28–like Protein Kinase," *J. Biol. Chem.* 266(6): 3402–3407 (1991).

Kharitonenkov et al., "A Family Of Proteins That Inhibit Signalling Through Tyrosine Kinase Receptors," *Nature* 386:181–186 (1997).

Abe et al., "Molecular Characterization of a Novel Metabotropic Glutamate Receptor mGluR5 Coupled to Inositol Pohosphate/$Ca^{2+}$ Signal," *J. Biol. Chem.* 267(19):13361–13368(1992).

Barford et al., "Crystal Structure of Human Protein Tyrosine Phosphatase 1B," *Science* 263: 1397–1403 (1994).

Beckman et al., "An Adhesive Domain Detected in Functionally Diverse Receptors," *Trends Biochem. Sci.* 18:40 (1993).

Bender et al., "AFC1, a LAMMER kinase from Arabidopsis thaliana, activates STE12–dependent processes in yeast," *Proc. Natl. Acad. Sci. USA* 91:12105–12109(1994).

Blaschuk et al., "Identification of a Conserved Region Common to Cadherins and Influenza Strain A. Hemagglutinins" *J. Mol. Biol.* 211, 679–682 (1990).

Brown–Shimer et al., "Molecular cloning and chromosome mapping of the human gene encoding protein phosphotyrosyl phosphatase 1B," *Proc. Natl. Acad. Sci. USA* 87:5148–5152 (1990).

Chao, "Growth Factor Signaling: Where is the Specificity?" *Cell* 68:995–997 (1992).

Ciossek et al., "Cloning, Characterization and Differential Expression of MDK2 and MDK5, Two Novel Receptor Tyrosine Kinases of the Eck/Eph Family," *Oncogene* 11:2085–2095 (1995).

Colwill et al., "The Clk/Sty Protein Kinase Phosphorylates SR Splicing Factors and Regulates Their Intranuclear Distribution," *The EMBO Journal* 15(2):265–275 (1996).

Cool et al., "DNA Isolated from a Human T–cell Library Encodes a Member of the Protein–tyrosine–phosphatase Family," *Proc. Natl. Acad. Sci. USA* 86, 5257–5761 (1989).

Cunningham et al., "Neural Cell Adhesion Molecule: Structure, immunoglobulin–Like Domains, Cell Surface Modulation, and Alternative RNA Splicing" *Science* 236, 799–806 (1987).

Curiel et al., "Gene Transfer to Respiratory Epithelial Cells via the Receptor–mediated Endocytosis Pathway," *Am. J. Respir. Cell. Mol. Biol.* 6, 247–252 (1992).

Duncan et al., "Alternative Splicing of STY, a Nuclear Dual Specificity Kinase*," *The Journal of Biological Chemistry* 270:21524–21531 (1995).

Eaton et al., "Construction and Characterization of an Active Factor VIII Variant Lacking the Central One–Third of the Molecule" *Biochemistry* 25(26) 8343–8347 (1986).

Fendly et al., "Characterization of Murine Monoclonal Antibodies Reactive to Either the Human Epidermal Growth Factor Receptor or HER2/neu Gene Product," *Cancer Research* 50, 1550–1558 (1990).

Field et al., Cloning and Characterization of CAP, the S. Cerevisiae Gene Encoding the 70 kd Adenylyl Clyclase–Associated Protein *Cell* 61:319–327 (1990).

Flores et al., "Nuclear Localization of the PEP Protein Tyrosine Phosphatase" *Mol. Cell. Biol.* 14:4938–4946 (1994).

Fry et al., "New Insights into Protein–tyrosine Kinase Receptor Signaling Complexes," *Protein Science* 2:1785–1797 (1993).

Fu, "The superfamily of arginine/serine–rich splicing factors," *RNA* 1:663–680(1995).

Garton et al., "A.J. and Tonks, N.K., PTP–PEST: a protein tyrosine phosphatase regulated by serine phosphorylation", *EMBO J.* 13:3763–3771 (1994).

Hammer et al., "Spontaneous Inflammatory Disease in Transgenic Rats Expressing HLA–B27 and Human $\beta_2$m: An Animal Model of HLA–B27–Associated Human Disorders," *Cell* 63, 1099–1112(1990).

Harada et al., "Selection of RNA–binding peptides in vivo," *Nature* 380:175–179 (1996).

Hedley et al., "An Amino Acid Sequence Motif Sufficient for Subnuclear Localization of an Arginine/Serine–rich Splicing Factor" *Proc. Natl. Acad. Sci. USA* 92:11524–11528 (1995).

Hillier et al., Accession No. R54222. Genbank database. The WashU–Merck EST Project (May 18, 1995).

Howell et al., "STY, a Tyrosine–Phoshorylating Enzyme with Sequence Homology to Serine/Threonine Kinases," *Molecular and Cellular Biology* 11(1):568–572 (1991).

Jiang et al., "The $\alpha$ Subunit of Merpron A" *J. of Biol Chem.* 267:9185 (1992).

Johnston et al., "Isolation of the Yeast Regulatory Gene Ga14 and Analysis of its Dosage Effects on the Galactose/melibiose Regulon," *Proc. Natl. Acad. Sci. USA* 79:6971–6975 (1982).

Kasprzak et al., "Location of a Contact Site Between Acting and Myosin in the Three–dimensional Structure of the Acto–S1 Complex," *Biochemistry* 28, 9230–9238 (1989).

Killen et al., "Specific Killing of Lymphocytes that Cause Experimental Autoimmune Myasthenia Gravis by Ricin Toxin–Acetylcholine Receptor Conjugates," *J. of Immunol.* 133(5) 2549–2553 (1984).

Kohtz et al., "Protein–protein interactions and 5'–splice–site recognition in mammalian mRNA precursors," *Nature* 368:119–124(1994).

Krueger et al., "A Human Transmembrane Protein–tyrosine–phosphatase, Ptp$\zeta$, Is Expressed in Brain and Has an N–terminal Receptor Domain Homologous to Carbonic Anhydrases," *Proc. Natl. Acad. Sci. USA* 89, 7417–7421 (1992).

Lammers et al., "Differential Activities of Protein Tyrosine Phosphatases in Intact Cells," *J. Biol. Chem.* 268, 22456–22462 (1993).

Lechner et al., "ERK6, a mitogen–activated protein kinase involved in C2C12 myoblast differentiation," *Proc. Natl. Acad. Sci. U.S.A.* 96:4355–4359 (1996).

Lu et al., "A human peptidyl–prolyl isomerase essential for regulation of mitosis," *Nature* 380:544–547 (1996).

Lutz et al., "The Distribution of Two hnRNP–Associated Proteins Defined by a Monoclonal Antibody Is Altered in Heat–Shocked HeLa Cells" *Exp. Cell Res.* 175, 109–124 (1988).

Matthews et al., "Characterization of Hematopoietic Intracellular Protein Tyrosine Phosphatases: Description of a Phosphatase Containing and SH2 Domain and Another Enriched in Proline–, Glutamic Acid, Serine–, and Threonine–Rich Sequences" *Mol. Cell Biol.* 12(5) 2396–2405 (1992).

Matviw et al., "Identification of a Human cDNA Encoding a Protein That Is Structurally and Functionally Related to the Yeast Adenylyl Cyclase–Associated CAP Proteins" *Mol. Cell Biol.* 12(11) 5033–5040 (1992).

Mauro et al., "Homophilic and Heterophilic Binding Activities of Nr–CAM, a Nervous System Cell Adhesion Molecule" *J. Cell Biol.* 119, 191–202 (1992).

McKnight, "Functional Relationships between Transcriptional Control Signals of the Thymidine Kinase Gene of Herpes Simplex Virus," *Cell* 31, 355–365 (1982).

Mermoud et al., "Regulation of mammalian spliceosome assembly by a protein phosphorylation mechanism," *EMBO J.* 13:5679–5688 (1994).

Millauer et al., "Globlastoma Growth Inhibited In Vivo by a Dominant–negative Flk–1 Mutant", *Nature* 367:576–579 (1994).

Mizuno et al., "Developmental Regulation of Gene Expression for the MPTPδ Isoforms in the Central Nervous System and the Immune System" *FEBS* 355, 223–228 (1994).

Nayler et al., "SAF–B Protein Couples Transcription and Pre–Mrna Splicing to SAR/MAR Elements" *Nucl. Acid. Res.* 26(15) 3542–3549 (1998).

Ota et al., Proc. Natl. Acad. Sci., 89, 2355–2359, Mar. 1992.

Redemann et al., "Anti–Oncogenic Activity of Signalling–Defective Epidermal Growth Factor Receptor Mutants," *Mol. and Cell. Biol.* 2(2) 491–498 (1992).

Rogers et al., "Amino Acid Sequences Conmmon to Rapidly Degraded Proteins: The PEST Hypothesis" *Science* 234:364–368 (1986).

Schlessinger and Ullrich, "Growth Factor Signalling by Receptor Tyrosine Kinases," *Neuron* 9:383–391 (1992).

Smith et al., "Single–step Purification of Polypeptides Expressed in *Escherichia Coli* as Fusion with Glutathione S–transferase" *Gene,* 67:31–40 (1988).

Staknis et al., "SR proteins promote the first specific recogntion of pre–mRNA and are present together with the U1 small nuclear ribonucleoprotein particle in a general splicing enhancer complex," *Mol. Cell. Biol.* 14:7670–7682 (1994).

Stein–Gerlach et al., "Protein–tyrosine Phosphate 1D Modulates Its Own State of Tyrosine Phosphorylation" *J. Biol. Chem.* 270:24635 (1995).

Stuckey et al., "Crystal Structure of Yersinia Protein Tyrosine Phospatase at 2.5 Å and the Complex with Tungstate" *Nature* 370:571–575 (1994).

Su et al., "The Crystal Structure of a Low–Molecular–Weight Phosphostyroisine Protein Phosphatase" *Nature* 370, 575–578 (1994).

Takekawa et al., "Cloning and characterization of a human cDNA encoding a novel putative cytoplasmic protein–tyrosine–phosphatase," *Biochem. Biophys. Res. Commun.* 189:1223–1230 (1992).

Thomas et al., "Structural Modification of Acidic Fibroblast Growth Factor Alter Activity, Stability, and Heparin Dependence" *Ann. NY Acad. Sci.* 9–17 (1991).

Ullrich et al., "Rat Insulin Genes: Construction of Plasmids Containing the Coding Sequences" *Science* 196:1313–1319 (1977).

Vogel et al., "Activation of a Phosphotyrosine Phosphatase by Tyrosine Phosphorylation," *Science* 259:1611–1614 (1994).

Vojtek et al., "Mammalian Ras Interacts Directly with the Serine/Threonine Kinase Raf," *Cell* 74:205–214 (1993).

Ward et al., "Construction and Characterisation of a Series of Multi–copy Promoter–probe Plasmid Vectors for Streptomyces Using the Aminoglycoside Phosphotransferase Gene from Tn5 as Indicator," *Mol. Gen. Genet.* 203, 468–478 (1986).

Yamauchi et al., "Epidermal Growth Factor Induced Association of the SHPTP2 Protein Tyrosine Phosphatase with a 115–kDa Phosphotyrosine Protein" *J. Biol Chem.* 270:14871–14874 (1995).

Yamauchi et al., "Identification of the Major SHPTP2–binding Protein That is Tyrosine–phosphorylated to Response in Insulin" *J. Biol. Chem.* 270:17716–17722 (1995).

Yun et al., "The Doa Locus Encodes a Member of a New Protein Kinase Family and is Essential for Eye and Embryonic Development in *Drosophila Melanogaster,* " *Genes & Development* 8: 1160–1173(1994).

Zahler et al., "SR Proteins: a Conserved Family of Pre–mRNA Splicing Factors," *Genes & Development* 6:837–847 (1992).

Zelicof et al., "Molecular Cloining and Characterization of a Rat Homolog of CAP, The Adenylyl Cyclase–Associated Protein From Saccharomyces Cervisiae" *J. of Biol. Chem.* 268(18) 13448–13453 (1993).

Zhang, et al., "Dissecting the Catalytic Mechanism of Protein Tyrosin Phosphatases" *Proc. Natl. Acad. Sci. USA* 91:1624–1627 (1994).

Dignam et al., "Accurate transcription initiation by RNA polymerase II in a soluble extract from Isolated mammalian nuclei," *Nucleic Acids Research*, 1983, pp. 1475–1489, vol. 11, No. 5.

Dingwall et al., "Nuclear targeting sequences –a consensus," *TIBS*, Dec. 1991, pp. 478–481, vol. 16.

Nelson et al., "Detection of acridinium esters by chemiluminexcence," *Nonistopic DNA Probe Tehcniques*, 1992, pp. 275–310.

*PCR Protocols: A Guide to Methods and Applications*, edited by Michael Innls et al., Academic Press, San Diego (1990) (Table of Contents Only).

Puissant et al., "An Improvement of the Single–Step Method of RNA Isolation by Acid Guanldinium Thiocyanate–Phenol–Chloroform Extraction," *BioTechniques*, 1990, pp. 148–149, vol. 8, No. 2.

Sambrook et al., *Molecular Cloning: A Laboratory Manual, 2nd Edition*, Cold Spring Harbor Laboratory Press (1989) (Table of Contents Only –All Three Volumes).

Sanger et al., "DNA sequencing with chain–terminating inhibitors," *Proc. Natl. Acad. Sci. USA*, Dec. 1977, pp. 5462–5467, vol. 74, No. 12.

FIG. 1

```
MCLK1    MRHSKRTYC-------PDWDERDWDYGTWRSSSSHKRKKRSHSSAREQKR      43
MCLK2    P.PR.YHSSERGSRGSYHEHYQSRKHKRRR.R.WSSSSDRTRRR.REDS        50
MCLK3    H.C..YRSPEPDPYLTYRWK.RRS.SREHEGRLRYPSR.EPPPR.S---        47
MCLK4    .......H.-------....S.ESWGHESY.G-.....R.....TQ.NRH       42

MCLK1    CRYDHSKTTDSYYLESRSINEKAYHSRRYVDEY--RNDYMGYEPGHPYGE       91
MCLK2    YHVRSRSSY.DHSSDR.LY-------D.RYCGSYR.....SRDRGEAY.DT      93
MCLK3    SRE.APYRTRKHAHHCHK.RTRSCSSASSRSQQSSKRSSR--------.        94
MCLK4    .KPH.QFKDSDCHYLEARCLNERDYRD.RYIDEY-.....CEGYVPRH.HR      91

MCLK1    PGSRYQMHS-SKSSGRSGRSSYKSKHRSRHHTSQHHSDGHSHRRKRSRSV      140
MCLK2    DFRQSYEYHREN..Y..Q...RRKHR.R.RRSRTFSRSSSHSS.RAK-..      142
MCLK3    SRE.APYRTRKHAHHCHK.RTRSCSSASSRSQQSSKRSSR--------.       136
MCLK4    DVESTYRIHC....V..R...P.R.RNRPCASH.S..--.........I       139

MCLK1    EDDEEGHLICQSGDVLSARYEIVDTLGEGAFGKVVECIDHKVGGRRVAVK      190
MCLK2    ...A.....YHV..W.QE.....S......TS.R..Q...RR..T....L.      192
MCLK3    ...K....V.RI.SW.QE.....GN....T........L..ARGKSQ..L.     186
MCLK4    ..............R.....................GMD.LH....          189

MCLK1    IVKNVDRYCEAAQSEIQVLEHLNTTDPHSTFRCVQMLEWFEHRGHICIVF      240
MCLK2    .I....EK.K...RL..N....KI..EK..KNKNL.....FD..DYH..M..S.  242
MCLK3    .IR..GH.R...RL..N...KKIKEK.KENK.L..L.SD.NFH..M..A.       236
MCLK4    .....GG.R...R........S....N.V.........D.H..V....        239

MCLK1    ELLGLSTYDFIKENSFLPFRMDHIRKMAYQICKSVNFLHSNKLTHTDLKP      290
MCLK2    .......F..L.D.NY..YPIHQV.H..F.L.QA.K...D............    292
MCLK3    ....KN.FE.L...N.Q.YPLP.V.H....L.HALR...E.Q.........     286
MCLK4    ...................QI....Q......Q.I....H.........      289

MCLK1    ENILFVKSDYTEANPKMKRDERTIVNPDIKVVDFGSATYDDEHHSTLVS       340
MCLK2    ......N...ELT..LEK.....SVKSTAVR.........F.H.....I..     342
MCLK3    ......N..EFETL..EHKSCE.KSVK.TSIR.A......F.H...T.I.A     336
MCLK4    ..........VVK..S........LK.T....................        339
                                                    ****
MCLK1    TRHYRAPEVILALGWSQPCDVWSIGCILIEYYLGFTVFPTHDSREHLAMM      390
MCLK2    ...........E..............IF..V...L.Q...N..........    392
MCLK3    .....P.....E...A...........F...R..L.Q....K.........    386
MCLK4    .............................Q...K.............       389
         **
MCLK1    ERILGPLPKHMIQKTRKRRYFHHDRLDWDEHSSAGRYVSRRCKPLKEFML      440
MCLK2    ......V.SR..R.....QK..YRG.......NT......REN....RRYLT   442
MCLK3    .K.....I.S...HR...QK..YKGG.V...N..D....KEN.....SY..    436
MCLK4    .......I.A...........K....NQ..............R........    439
                                                 <
MCLK1    SQDAEHEFLFDLVGKILEYDPAKRITLKEALKHPFFYPLKKHT             483
MCLK2    .EAED.HQ....IENM...E....L..G...Q....AC.RTEPPNTKLWD     492
MCLK4    QDSL..VQ.....MRRM..F...Q....A...L...AG.TPEERSFHSSSR    486
MCLK5    CHDE...K......RRM.......R...D...Q....DL..RK            489

MCLK1
MCLK2    SSRDISR                                                 499
MCLK3    NPSR                                                    496
MCLK4
```

FIG. 2

MPHPRRYHSSERGSRGSYHEHYQSRKHKRRRSRSWSSSSDRTRRRRREDSYHV
RSRSSYDDHSSDRRLYDRRYCGSYRRNDYSRDRGEAYYDTDFRQSYEYHRENS
SYRSQRSSRRKHRRRRRRSRTFSRSSSHSSRRAKSVEDDAEGHLIYHVGDWLQE
RYEIVSTLGEGTSGRVVQCVDHRRGGTRVALKIIKNVEKYKEAARLEINVLEKI
NEKDPDNKNLCVQMFDWFDYHGHMCISFELLGLSTFDFLKDNNYLPYPIHQ
VRHMAFQLCQAVKFLHDNKLTHTDLKPENILFVNSDYELTYNLEKKRDERSV
KSTAVRVVDFGSATFDHEHHSTIVSTRHYRAPEVILELGWSQPCDVWSIGCIIFE
YYVGFTLFQTHDNREHLAMMERILGPVPSRMIRKTRKQKYFYRGRLDWDENT
SAGRYVRENCKPLRRYLTSEAEDHHQLFDLIENMLEYEPAKRLTLGEALQHPF
FACLRTEPPNTKLWDSSRDISR

FIG. 3

```
   1 cgcacgggcc tcgccgccag aacgatgccc catccccgaa ggtaccattc ctcagagcga
  61 ggtagccggg ggagttacca cgaacactat cagagccgaa agcataagcg aagaagaagt
 121 cgctcctggt caagtagcag tgaccggaca aggcggcggc ggagggagga cagctaccac
 181 gttcggtccc gaagcagcta tgatgaccat tcgtccgatc ggcggctgta cgatcggcgg
 241 tactgtggca gctacaggcg caatgactac agccgggaca gaggggaggc ttactacgac
 301 acagactttc ggcagtccta tgaataccat cgagagaaca gcagttaccg aagccagcgc
 361 agcagccgaa ggaaacacag aaggcggagg agacggagcc ggacattcag ccgctcatct
 421 tcacacagca gccggagagc caagagtgta gaggacgacg ctgagggcca cctcatctac
 481 cacgtcgggg actggctaca agagcgatat gaaattgtaa gcaccttagg agaagggact
 541 tcgggccgag ttgtgcagtg tgtggaccat cgcaggggcg gaacacgagt tgccctgaag
 601 atcattaaga atgtggagaa gtacaaggaa gcagcccgac tagaaatcaa cgtgctggag
 661 aaaatcaatg agaaagatcc tgacaacaag aacctctgtg tccagatgtt tgactggttt
 721 gactaccatg gccacatgtg tatctccttt gagcttctgg gccttagcac cttcgatttc
 781 ctcaaagaca acaactacct gccctacccc atccaccaag tgcgccacat ggccttccag
 841 ctctgccagg ccgtcaagtt cctccatgat aacaagttga cacatacgga cctcaaacct
 901 gaaaatattc tgtttgtgaa ttcagactac gaactcacct acaacctaga gaagaagcga
 961 gatgagcgca gtgtaaagag cacagccgtg cgggtggtgg acttcggcag tgccacccttt
1021 gaccacgaac accatagcac cattgtctcc actcgccatt accgagcccc cgaggtcatc
1081 ctggagttgg gctggtcaca gccatgcgat gtatggagca taggctgcat catctttgag
1141 tactacgttg gcttcaccct cttccagacc catgacaaca gagagcatct agccatgatg
1201 gaaaggatcc tgggtcctgt cccttctcgg atgatcagaa agacaagaaa acagaaatat
1261 ttttatcggg gtcgcctgga ttgggatgag aacacctcag ccggccgcta cgttcgtgag
1321 aactgcaaac ctctgcggcg gtatctgacc tcagaggcag aggaccacca ccagctcttc
1381 gatctgattg aaaatatgct agagtatgag cctgctaagc ggctgacctt aggtgaagcc
1441 cttcagcatc ctttcttcgc ctgccttcgg actgagccac ccaacaccaa gttgtgggac
1501 tccagtcggg atatcagtcg gtgacaatta ggctgggc
```

FIG. 4

MHHCKRYRSPEPDPYLTYRWKRRRSYSREHEGRLRYPSRREPPPRRSRSRSHDR
IPYQRRYREHRDSDTYRCEERSPSFGEDCYGSSRSRHRRRSRERAPYRTRKHAH
HCHKRRTRSCSSASSRSQQSSKRSSRSVEDDKEGHLVCRIGDWLQERYEIVGNL
GEGTFGKVVECLDHARGKSQVALKIIRNVGKYREAARLEINVLKKIKEKDKEN
KFLCVLMSDWFNFHGHMCIAFELLGKNTFEFLKENNFQPYPLPHVRHMAYQ
LCHALRFLHENQLTHTDLKPENILFVNSEFETLYNEHKSCEEKSVKNTSIRVAD
FGSATFDHEHHTTIVATRHYRPPEVILELGWAQPCDVWSIGCILFEYYRGFTLF
QTHENREHLVMMEKILGPIPSHMIHRTRKQKYFYKGGLVWDENSSDGRYVKE
NCKPLKSYMLQDSLEHVQLFDLMRRMLEFDPAQRITLAEALLHPFFAGLTPEE
RSFHSSRNPSR

FIG. 5

```
   1 ctgcaggtcg acactagtgg atccaaagaa ttcggcacga gcgcagccgg agcctgggag
  61 acgatgcatc actgtaagcg ataccgttcc ccagagccag acccatacct gacgtaccgc
 121 tggaagagga ggcggtctta cagtcgggag catgaaggtc gactacgata cccatcccga
 181 agggagcctc ccccacggag atcacggtcc agaagccatg atcgtatacc ctaccagcgg
 241 aggtaccggg aacaccgtga cagtgatacg tatcggtgtg aagagcggag cccatctttt
 301 ggagaggact gctatgggtc ttcacgttct gcacatcgga gacggtcacg agagagggcg
 361 ccgtaccgta cccgcaagca tgcccaccac tgtcacaaac gccgtaccag gtcttgtagc
 421 agtgcttcct cgagaagcca acagagcagt aagcgcagca gccggagtgt ggaagatgac
 481 aaggagggcc acctggtgtg ccggatcggc gattggctcc aagagcgata tgagatcgtg
 541 gggaacctgg gtgaaggcac ctttggcaag gtggtggagt gcttggacca tgccagaggg
 601 aagtcacagg ttgccctgaa gatcatccgt aatgtgggca agtatcggga agctgctcgt
 661 ctagaaatta atgttctcaa gaaaatcaag gagaagacaa ggaaaataa gttcctttgt
 721 gtcctgatgt ctgactggtt caacttccat ggtcatatgt gcatcgcctt tgagctcctg
 781 ggcaagaaca cctttgagtt cctgaaggag aacaacttcc agccttaccc cctaccacat
 841 gtccggcaca tggcctacca gctctgtcat gcccttagat tctacacga gaaccagctg
 901 acccacacag acttgaagcc agagaacatc ttgtttgtga attctgagtt tgaaaccctc
 961 tacaatgagc acaagagctg cgaggagaag tcagtgaaga acaccagcat ccgagtggca
1021 gactttggca gtgccacgtt tgaccatgaa catcacacca ccattgtggc cacccgtcac
1081 taccgcccac ctgaggtgat ccttgagctg ggctgggcac agccttgtga tgtctggagt
1141 atcggctgca ttctctttga gtactaccgt ggctttacac tcttccagac ccatgaaaat
1201 agagaacact tggttatgat ggagaagatt ctaggaccca tcccatcaca catgatccac
1261 cgtaccagga agcagaaata tttctacaaa ggggcctgg tttgggatga aacagctct
1321 gatgggcggt atgtgaagga gaactgcaaa cctctgaaga gttacatgct gcaggactcc
1381 ctggagcatg tgcagctgtt tgacctgatg aggaggatgt tagagttcga ccctgctcag
1441 cgcatcacat tggcagaagc cttgctgcac cccttctttg ctggcctgac ccctgaggag
1501 cggtccttcc acagcagccg taaccccagc agatgacagg tgcaggccag cacacgaaga
1561 gttggagagc tggactgggc tgctggcccc ttttctccag cctctcccac tggcctcaga
1621 gccagagcca ccgatgaaca gtgcaatgtg aaggaaggca ggacctgcaa gggaaggggg
1681 aatgtggtgc ccggctgcca gaaagcacag attggaccca agctttata tgttgtaaag
1741 ttataataaa gtgtttctta ctgtttgtaa aaaaaaaaa aaaaaaa
```

FIG. 6

MRHSKRTHCPDWDSRESWGHESYSGSHKRKRRSHSSTQENRHCKPHHQFKD
SDCHYLEARCLNERDYRDRRYIDEYRNDYCEGYVPRHYHRDVESTYRIHCSKS
SVRSRRSSPKRKRNRPCASHQSHSKSHRRKRSRSIEDDEEGHLICQSGDVLRAR
YEIVDTLGEGAFGKVVECIDHGMDGLHVAVKIVKNVGRYREAARSEIQVLEH
LNSTDPNSVFRCVQMLEWFDHHGHVCIVFELLGLSTYDFIKENSFLPFQIDHIR
QMAYQICQSINFLHHNKLTHTDLKPENILFVKSDYVVKYNSKMKRDERTLKN
TDIKVVDFGSATYDDEHHSTLVSTRHYRAPEVILALGWSQPCDVWSIGCILIEY
YLGFTVFQTHDSKEHLAMMERILGPIPAHMIQKTRKRKYFHHNQLDWDEHSS
AGRYVRRRCKPLKEFMLCHDEEHEKLFDLVRRMLEYDPARRITLDEALQHPFF
DLLKRK

FIG. 7

```
   1 aaagagacgc agcggctgga gaggaacgac ggcggtttgg cgacatttct gcccaaaagg
  61 ccgcttgctt ttgcggagat gcggcattcc aaacgaactc actgtcctga ttgggatagt
 121 agagaaagct ggggccatga aagctacagt ggaagtcaca aacgcaagag aaggtctcac
 181 agcagtactc aggagaacag gcactgtaaa ccacatcatc agtttaaaga ctcggattgt
 241 cactatttag aagcaagatg cttgaatgag agagattatc gggaccggag atacattgat
 301 gaatacagaa atgactactg cgaaggatat gttccaagac attaccatag agacgttgaa
 361 agcacttacc ggatccattg cagtaaatcc tcagtcagga gcaggagaag cagccctaag
 421 agaaagcgta atagaccctg tgcaagtcat cagtcgcatt cgaagagcca ccgaaggaaa
 481 agatccagga gtatagagga tgatgaggag ggtcacctga tctgtcaaag tggagacgtt
 541 ctaagagcaa gatatgaaat cgtggacact ttaggtgaag gagcctttgg caaagttgta
 601 gagtgcattg atcacggcat ggatggctta catgtagcag tgaaaattgt aaaaaatgta
 661 ggacgttacc gggaggcagc tcgttctgaa atccaagtat tggagcactt gaacagcact
 721 gaccccaaca gtgtcttccg atgcgtccag atgctagagt ggtttgatca tcatggtcat
 781 gtttgtattg tgtttgagct gctgggactt agtacctatg attttattaa agaaaatagt
 841 tttctgccat ttcaaattga tcacatcagg caaatggctt atcagatctg ccagtctata
 901 aattttttac atcataataa attaacacac acggacctaa aacctgaaaa tatttatttt
 961 gtgaagtctg actatgtagt caaatacaat tctaaaatga aacgagatga gcgcacattg
1021 aaaaacacag atatcaaagt tgttgatttt ggaagtgcaa catatgacga cgaacatcat
1081 agtactttgg tgtccacaag gcactacagg gctccagagg tcattttggc tctaggttgg
1141 tctcagcctt gtgatgtttg gagcataggc tgcattctta ttgagtacta ccttgggttc
1201 acagtctttc agacccacga tagtaaagag cacctggcaa tgatggagcg gatcttagga
1261 cccatcccag cacatatgat ccagaagaca aggaaacgca agtatttcca ccataaccag
1321 ctagattggg acgagcatag ttcagctggg agatatgtta ggagacgctg caagccgtta
1381 aaggaattta tgctgtgtca tgacgaagag catgagaagc tgtttgacct ggttcgaaga
1441 atgttggagt atgacccagc gagaaggatc accttggatg aagcattgca gcacccttc
1501 tttgacttat taaaaaggaa atgagtggga gtcagggcgg ccgcaccgc
```

NUCLEIC ACID ENCODING CLK2 PROTEIN KINASES

RELATED APPLICATION

This application claims the benefit and is a continuation of the U.S. patent application Ser. No. 09/127,248, filed Jul. 31, 1998, now abandoned by Axel Ullrich and Oliver Nayler, and entitled NUCLEIC ACIDS ENCODING CLK PROTEIN KINASES and claims the benefit of and which is a continuation-in-part of the U.S. patent application Ser. No. 08/877,150, filed Jun. 17, 1997, by Axel Ullrich and Oliver Nayler, and entitled "NOVEL PTP20, PCP-2, BDP-1, CLK, AND SIRP PROTEINS AND RELATED PRODUCTS AND METHODS", and claims the benefit of U.S. Provisional Patent Application Serial No. 60/034,286, filed Dec. 19, 1996, by Axel Ulirich and Oliver Nayler, and entitled "CLK PROTEIN KINASES AND RELATED PRODUCTS AND METHODS", all of which are incorporated by reference herein in their entirety including all figures, tables, and drawings.

INTRODUCTION

The present invention relates to novel CDC2 like protein kinases (CLK protein kinases). These protein kinases phosphorylate proteins rich in serine and arginine.

BACKGROUND OF THE INVENTION

The following description of the background of the invention is provided to aid in understanding the invention, but is not admitted to be or describe prior art to the invention.

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins. Enzymes that mediate phosphorylation of cellular effectors fall into two classes. While protein phosphatases hydrolyze phosphate moieties from phosphoryl protein substrates, protein kinases transfer a phosphate moiety from adenosine triphosphate to protein substrates. The converse functions of protein kinases and protein phosphatases balance and regulate the flow of signals in signal transduction processes.

Protein kinases and protein phosphatases are typically divided into two groups: receptor and non-receptor type proteins. Receptor protein kinases are comprised of an extracellular domain, a membrane spanning region, and a catalytic domain.

Protein kinases and protein phosphatases are divided further into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Membrane association is an important feature of signal transduction. Protein kinases propagate extracellular signals to the inside of the cell by attracting other signaling molecules to the membrane. Schlessinger and Ullrich, 1992, *Neuron* 9:383–391. For instance, many receptor protein kinases bind an extracellular ligand, dimerize, and cross phosphorylate one another. These phosphate moieties subsequently attract other proteins necessary for propagating the signal within the cell. The molecules that signal downstream of the receptor protein kinases are often nonreceptor protein kinases which propagate and amplify the extracellular signal.

A class of non-receptor protein kinases are implicated in regulating RNA splicing. Fu, 1995 *RNA* 1:663–680; Staknis and Reed, 1994, *Mol. Cell. Biol.* 14:7670–7682. These protein kinases phosphorylate polypeptides rich in serine and arginine (SR proteins). SR proteins are characterized as containing at least one amino-terminal RNA recognition motif and a basic carboxyterminal domain rich in serine and arginine residues, often arranged in tandem repeats. Zahler et al., 1992, *Genes Dev* 6:837–847. Experimental evidence supports the idea that the SR domain is involved in protein—protein interactions (Kohtz et al., 1994, *Nature* 368:119–124) as well as protein-RNA interactions (Harada et al., 1996, *Nature* 380:175–179), and may contribute to a localization signal directing proteins to nuclear speckles. Hedley et al., 1995, *Proc. Natl. Acad. Sci. USA* 92:11524–11528.

A recent report demonstrated mCLK1, a CDC2 like kinase, interacts with ASF/SF2, SRp20 and hnRNP proteins in a yeast two hybrid system. Because hnRNP-K binds to the protooncogene $p95^{vav}$, mCLK1 could be implicated in transmitting signals that regulate the expression of the protooncogenes myc and fos in hematopoietic cells. Furthermore, it was demonstrated, that mCLK1 could phosphorylate ASF/SF2 in vitro, suggesting, that SR containing proteins are the natural substrates of mCLK1. Colwill et al., 1996, *EMBO J.* 15:265–275.

mCLK1 is a dual specificity protein kinase originally isolated in mouse expression libraries (Ben-David et al., 1991, *EMBO J.* 10:317–325; Howell et al., 1991, *Mol. Cell. Biol.* 11:568–572) and human (hCLK1, hCLK2, hCLK3), plant (AFC1, AFC2, AFC3) and fly (DOA) CLK protein kinases have since been identified. Johnson and Smith, 1991, *J. Biol. Chem.* 266:3402–3407; Hanes et al., 1994, *J. Mol. Biol.* 244:665–672; Bender and Fink, 1994, *Proc. Natl. Acad. Sci. USA* 91:12105–12109; Yun et al., 1994, *Genes. Dev.* 8:1160–1173. The amino terminal domain of these proteins is rich in serine and arginine, whereas the catalytic domain can be most similar to CDC2, a serine/threonine protein kinase. Ben-David et al., 1991, *EMBO J.* 10:317–325.

Both mCLK1 and the Drosophila homologue, DOA, regulate RNA splicing events. Each of these have two alternatively spliced products coding for either the full-length catalytically active protein or a truncated protein lacking the catalytic domain. Yun et al., 1994, *Genes. Dev.* 8:1160–1173; Duncan et al., 1995, *J. Biol. Chem.* 270:21524–21531. Identical splice forms were also found in human CLK protein kinases. Hanes et al., 1994, *J. Mol. Biol.* 244:665–672. The ratio of these splice products appears to be developmentally regulated in Drosophila (Yun et al., 1994, *Genes. Dev.* 8:1160–1173), and in a tissue and cell type specific manner in mammals. Hanes et al., 1994, *J. Mol. Biol.* 244:665–672; Duncan et al., 1995, *J. Biol. Chem.* 270:21524–21531. In addition, the expression of several other, larger transcripts, are observed to be differentially regulated and are shown to represent partially spliced products. Duncan et al., 1995, *J. Biol. Chem.* 270:21524–21531.

SUMMARY OF THE INVENTION

The present invention is based in part upon the isolation and characterization of nucleic acid molecules encoding CLK serine/threonine kinases designated mCLK2, mCLK3, and mCLK4. CLK serine/threonine kinases regulate RNA splicing in cells and some are highly expressed in cancer cells as well as testis. Various mCLK2, mCLK3, and mCLK4 related molecules and compounds can now be designed as treatments of cancers or as contraceptives to reproduction in male organisms.

The present invention is based in part upon nucleic acid molecules encoding novel mCLK2, mCLK3, and mCLK4 polypeptides, nucleic acid molecules encoding portions of their amino acid sequences, nucleic acid vectors harboring such nucleic acid molecules, cells containing such nucleic acid vectors, purified polypeptides encoded by such nucleic acid molecules, and antibodies to such polypeptides, and methods of identifying compounds that bind mCLK2, mCLK3, and mCLK4 or abrogate their interactions with natural binding partners. Also disclosed are methods for diagnosing and treating specific abnormal conditions in an organism with mCLK2, mCLK3, and mCLK4 related molecules or compounds. The nucleic acid molecules, nucleic acid vectors, recombinant cells, polypeptides, and antibodies may be produced using well known and standard techniques used currently in the art.

Thus in a first aspect, the invention features isolated, enriched, or purified nucleic acid molecules encoding a novel mCLK2, mCLK3, or mCLK4 polypeptide.

The term "isolated", in reference to nucleic acid molecules, indicates that a naturally occurring sequence has been removed from its normal cellular environment. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched", in reference to nucleic acid molecules, means that the specific DNA or RNA sequence constitutes a significantly higher fraction (2–5 fold) of the total DNA or RNA present in the cells or solution of interest than in normal or diseased cells or in the cells from which the sequence was taken. A person skilled in the art could enrich a nucleic acid mixture by preferentially reducing the amount of other DNA or RNA present, or preferentially increasing the amount of the specific DNA or RNA, or both. However, nucleic acid molecule enrichment does not imply that there is no other DNA or RNA present, the term only indicates that the relative amount of the sequence of interest has been significantly increased. The term "significantly" qualifies "increased" to indicate that the level of increase is useful to the person performing the recombinant DNA technique, and generally means an increase relative to other nucleic acids of at least 2 fold, or more preferably at least 5 to 10 fold or more. The term also does not imply that there is no DNA or RNA from other sources. Other DNA may, for example, comprise DNA from a yeast or bacterial genome, or a cloning vector. In addition, levels of mRNA may be naturally increased relative to other species of mRNA when working with viral infection or tumor growth techniques. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process, which includes the construction of a cDNA library from mRNA and isolation of distinct cDNA clones, yields an approximately $10^6$-fold purification of the native message. Thus, purification of at least one order of magnitude, preferably two or three orders, and more preferably four or five orders of magnitude is expressly contemplated.

The term "nucleic acid molecule" describes a polymer of deoxyribonucleotides (DNA) or ribonucleotides (RNA) The nucleic acid molecule may be isolated from a natural source by cDNA cloning or subtractive hybridization or synthesized manually. The nucleic acid molecule may be synthesized manually by the triester synthetic method or by using an automated DNA synthesizer.

"cDNA cloning" techniques refer to hybridizing a small nucleic acid molecule, a probe, to genomic cDNA that is bound to a membrane. The probe hybridizes (binds) to complementary sequences of cDNA. The term "complementary" describes two nucleotides that can form multiple favorable interactions with one another. For example, adenine is complementary to thymidine as they can form two hydrogen bonds. Similarly, guanine and cytosine are complementary since they can form three hydrogen bonds. cDNAs are molecules that are reverse transcribed from fragments of message RNA from a genomic source. These fragments form a cDNA library of nucleic acid molecules. cDNA libraries are constructed from natural sources such as mammalian blood, semen, or tissue.

The term "subtractive hybridization" refers to a method similar to cDNA-cloning except that cDNA prepared from mRNA in unstimulated cells is added to mRNA in stimulated or different types of cells. cDNA/mRNA can then be precipitated to enrich the mRNA specific to the stimulation signal or different cell.

The term "hybridize" refers to a method of interacting a nucleic acid probe with a DNA or RNA molecule in solution or on a solid support, such as cellulose or nitrocellulose. If a nucleic acid probe binds to the DNA or RNA molecule with high affinity, it is said to "hybridize" to the DNA or RNA molecule. As mentioned above, the strength of the interaction between the probe and its target can be assessed by varying the stringency of the hybridization conditions. Various low or high stringency hybridization conditions may be used depending upon the specificity and selectivity desired. Stringency is controlled by varying salt or denaturant concentrations. Under stringent hybridization conditions only highly complementary nucleic acid sequences hybridize. Preferably, such conditions prevent hybridization of nucleic acids having one or two mismatches out of 20 contiguous nucleotides.

By "novel" is meant new and in the particular context of the present invention refers to CLK sequences that have not been previously described. In preferred embodiments the novel sequence may be the full-length serine CLK2 or CLK3 sequence, the full-length mammalian CLK4 sequence, or shorter fragments (preferably functional fragments) if any of the above as long as they were not already previously described.

The terms "mCLK2", "mCLK3", and "mCLK4" refer to polypeptides that have amino acid sequences substantially similar to those set forth in FIG. 1, FIG. 2, FIG. 4, or FIG. 6. A sequence that is substantially similar will preferably have at least 95% identity, more preferably at least 96–97% identity, and most preferably 98–100% identity to the sequence set forth in FIG. 1, FIG. 2, FIG. 4, or FIG. 6. CLK protein kinase polypeptides preferably have protein kinase activity and fragments of the full length CLK protein kinase sequences having such activity may be identified using techniques well known in the art, such as sequence comparisons and assays such as those described in the examples herein. Other aspects of mCLK2, mCLK3, and mCLK4 nucleic acid sequences, amino acid sequences, functions and properties are further depicted in Nayler et al., 1997, Biochem J. 326: 693–700, hereby incorporated by reference herein in its entirety including all figures, tables, and drawings.

By "identity" is meant a property of sequences that measures their similarity or relationship. Generally speaking, identity is measured by dividing the number of identical residues by the total number of residues and gaps and multiplying the product by 100. "Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity.

A preferred embodiment of the invention concerns nucleic acid molecules relating to mCLK2, mCLK3, and mCLK4 that are enriched, isolated, or purified from a mammalian source. These nucleic acid molecules can be isolated from, among others, blood, semen, or tissue. Although mCLK2, mCLK3, and mCLK4 nucleic acid molecules are isolated from mouse cells, current recombinant DNA techniques can readily elucidate related nucleic acid molecules in other mammalian tissue. Mammals include, but are not limited to, mice, rats, rabbits, cows, horses, monkeys, apes, and preferably humans.

Another preferred embodiment of the invention concerns isolated nucleic acid molecules that encode at least seventeen amino acids of a mCLK2, mCLK3, or mCLK4 polypeptide. Preferably, at least 17, 20, 25, 30, 35, 40, 50, 100, 200, 300, 400, 450, 475, or 485 contiguous amino acids are encoded. This preferred embodiment of the invention is achieved by applying routine recombinant DNA techniques known to those skilled in the art.

Another aspect of the invention features a nucleic acid probe that can detect nucleic acid molecules encoding a mCLK2, mCLK3, or mCLK4 polypeptide in a sample.

The term "nucleic-acid probe" refers to a nucleic acid molecule that is complementary to and can bind a nucleic acid sequence encoding the amino acid sequence substantially similar to that set forth in FIG. 1, FIG. 2, FIG. 4, or FIG. 6.

The nucleic acid probe or its complement encodes any one of the amino acid molecules set forth in the invention. Thus the nucleic acid probe can encode at least 17, 20, 25, 30, 35, 40, 50, 100, 200, 300, 400, 450, 475, or 485 contiguous amino acids of the full-length sequence set forth in FIG. 1, FIG. 2, FIG. 4, or FIG. 6.

The nucleic acid probe can be labeled with a reporter molecule or molecules. The term "reporter molecule" refers to a molecule that is conjugated to the nucleic acid probe or is contained within the nucleic acid probe. The reporter molecule allows the detection of the probe by methods used in the art. Reporter molecules are chosen from, but not limited to, the group consisting of an enzyme, such as a peroxidase, a radioactive element, or an avidin or biotin molecule.

A nucleic acid probe, whether labeled or unlabeled, should hybridize to a complement in a sample. Various low or high stringency hybridization conditions may be used depending upon the specificity and selectivity desired. Stringency is controlled by varying salt or denaturant concentrations. Under stringent hybridization conditions only highly complementary nucleic acid sequences hybridize. Preferably, such conditions prevent hybridization of nucleic acid molecules having one or two mismatches out of 20 contiguous nucleotides, more preferably prevent hybridization of nucleic acid molecules having one mismatch out of 35 contiguous nucleotides, and most preferably prevent hybridization of nucleic acid molecules having one mismatch out of 50 contiguous nucleotides.

The nucleic acid probe or complement can also refer to a nucleic acid molecule encoding a conserved or unique region of amino acids. These nucleic acid molecules are useful as hybridization probes to identify and clone additional polypeptides relating to CLK serine/threonine kinases. The term "conserved nucleic acid regions" refers to regions present in two or more nucleic acid molecules encoding a CLK protein kinase polypeptide, to which a particular nucleic acid sequence can hybridize under lower stringency conditions. Examples of lower stringency conditions suitable for screening nucleic acid molecules are provided in Abe, et al. *J. Biol. Chem.*, 19:13361 (1992) (hereby incorporated by reference herein in its entirety, including any drawings). Preferably, conserved regions differ by no more than 5 out of 20 nucleotides, more preferably conserved regions differ by no more than 10 out of 20 nucleotides, and most preferably conserved regions differ by no more than 15 out of 20 nucleotides. Protein kinases share conserved regions in the catalytic domain.

The term "unique nucleic acid region" concerns a sequence present in a full length nucleic acid molecule encoding a CLK protein kinase polypeptide that is not present in a sequence encoding any other naturally occurring polypeptide. Such regions preferably comprise 30 or 45 contiguous nucleotides, more preferably 100 contiguous nucleotides, and most preferably 200 contiguous nucleotides present in the full length nucleic acid sequence encoding a CLK protein kinase polypeptide. In particular, a unique nucleic acid region is preferably of mammalian origin.

Methods for using the probes include detecting the presence or amount of CLK protein kinase RNA in a sample by contacting the sample with a nucleic acid probe under conditions such that hybridization occurs and detecting the presence or amount of the probe bound to CLK RNA. The nucleic acid duplex formed between the probe and a nucleic acid sequence encoding a CLK protein kinase polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container holding a nucleic acid probe.

In yet another aspect, the invention relates to a nucleic acid vector comprising a promoter element and a nucleic acid molecule described in the first aspect of the invention.

The term "nucleic acid vector" relates to a single or double stranded circular nucleic acid molecule that can be transfected or transformed into cells and replicate independently or within a cell genome. A vector can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule encoding a CLK protein kinase can be inserted into a vector by cutting the vector with restriction enzymes and ligating the two pieces together.

The term "promoter element" describes a nucleotide sequence that is incorporated into a vector that, once inside an appropriate cell, may facilitate transcription factor and/or polymerase binding and subsequent transcription of portions of the vector DNA into mRNA. The promoter element precedes the SI end of the nucleic acid molecule of the first aspect of the invention such that the latter is transcribed into mRNA. Recombinant cell machinery then translates mRNA into a polypeptide.

Many techniques are available to those skilled in the art to facilitate transformation or transfection of the nucleic acid vector into a prokaryotic or eukaryotic organism. The terms "transformation" and "transfection" refer to methods of inserting a nucleic acid vector into a cellular organism. These methods involve a variety of techniques, such as treating the cells with high concentrations of salt, an electric field, or detergent, to render the cell outer membrane or wall permeable to nucleic acid molecules of interest.

A nucleic acid vector can be useful for identifying natural binding partners of CLK serine/threonine kinases.

The term "natural binding partners" refers to polypeptides that bind to CLK serine/threonine kinases and play a role in propagating a signal in a signal transduction process. The term "natural binding partner" also refers to a polypeptide that binds to CLK serine/threonine kinases within a cellular environment with high affinity. High affinity represents an equilibrium binding constant on the order of 10-1 M. However, a natural binding partner can also transiently interact with a CLK protein kinase and chemically modify it. CLK protein kinase natural binding partners are chosen from a group consisting of, but not limited to, src homology 2 (SH2) or 3 (SH3) domains, other phosphoryl tyrosine binding domains, and receptor and non-receptor protein kinases or protein, phosphatases.

Methods are readily available in the art for identifying binding partners of polypeptides of interest. These methods include screening cDNA libraries included in one nucleic acid vector with a nucleic acid molecule encoding the desired polypeptide in another nucleic acid vector. Vojtek et al., 1993, Cell 74:205–214. These techniques often utilize yeast recombinant cells. These techniques also utilize two halves of a transcription factor, one half that is fused to a polypeptide encoded by the cDNA library and the other that is fused to the polypeptide of interest. Interactions between a polypeptide encoded by the cDNA library and the polypeptide of interest are detected when their interaction concomitantly brings together the two halves into an active transcription factor which in turn activates a gene that reports the interaction. Any of the nucleic molecules encoding mCLK2, mCLK3, or mCLK4 can be readily incorporated into an nucleic acid vector used in such a screening procedure by utilizing standard recombinant DNA techniques in the art.

Another aspect of the invention relates to a recombinant cell or tissue comprising a nucleic acid molecule encoding a mCLK2, mCLK3, or mCLK4 polypeptide.

The term "recombinant" refers to an organism that has a new combination of genes or nucleic acid molecules. A new combination of genes or nucleic acid molecules can be introduced to an organism using a wide array of nucleic acid manipulation techniques available to those skilled in the art.

The recombinant cell can be a eukaryotic or prokaryotic organism. The term "eukaryote" refers to an organism comprised of cells containing a nucleus. Eukaryotes are differentiated from "prokaryotes" which do not house their genomic DNA inside a nucleus. Prokaryotes include unicellular organisms such as bacteria while eukaryotes are represented by yeast, invertebrates, and vertebrates.

The recombinant cell can also harbor a nucleic acid vector that is extragenomic. The term "extragenomic" refers to a nucleic acid vector which does not integrate into a cell genome. Many nucleic acid vectors are designed with their own origins of replication which allow them to utilize the recombinant cell replication machinery to copy and propagate the nucleic acid vector nucleic acid sequence. These nucleic acid vectors are small enough that they are not likely to harbor nucleic acid sequences homologous to genomic sequences of the recombinant cell. Thus these nucleic acid vectors replicate independently of the genome and do not recombine with or integrate into the genome.

A recombinant cell can also harbor a portion of a nucleic acid vector in an intragenomic fashion. The term "intragenomic" defines a nucleic acid vector that integrates within a cell genome. Multiple nucleic acid vectors available to those skilled in the art contain nucleic acid sequences that are homologous to nucleic acid sequences in a particular organism's genomic DNA. These homologous sequences will result in recombination events that incorporate portions of the nucleic acid vector into the genomic DNA. Those skilled in the art can control which nucleic acid sequences of the nucleic acid vector integrate into the cell genome by flanking the portion to be integrated into the genome with homologous sequences in the nucleic acid vector.

In yet another aspect, the invention features an isolated, enriched, or purified polypeptide encoded by a mCLK2, mCLK3, or mCLK4 nucleic acid molecule of the invention.

The term "isolated", in reference to a polypeptide, describes a polymer of amino acids conjugated to each other that are separated from a natural source. The polypeptide can also be synthesized manually. Isolated peptides can be at least 17, 20, 25, 30, 35, 40, 50, 100, 200, or 300 contiguous amino acids of one of the full-length sequences set forth in FIG. 1, FIG. 2, FIG. 4, or FIG. 6. In certain aspects longer polypeptides are preferred, such as those with 400, 450, 475, or 485 of the contiguous amino acids of mCLK2, mCLK3, or mCLK4 set forth in FIG. 1, FIG. 2, FIG. 4, or FIG. 6.

The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not-imply that the sequence is the only amino acid chain present, but that it is essentially free (about 90–95% pure at least) of non-amino aced material naturally associated with it.

The term "enriched", in reference to a polypeptide, defines a specific amino acid sequence constituting a significantly higher fraction (2–5 fold) of the total of amino acids present in the cells or solution of interest than in normal or diseased cells or in the cells from which the sequence was separated. A person skilled in the art can preferentially reduce the amount of other amino acid sequences present, or preferentially increase the amount of specific amino acid sequences of interest, or both. However, the term "enriched" does not imply that there are no other amino acid sequences present. Enriched simply means the relative amount of the sequence of interest has been significantly increased. The term "significant" indicates that the level of increase is useful to the person making such an increase. The term also means an increase relative to other amino acids of at least 2 fold, or more preferably at least 5 to 10 fold, or even more. The term also does not imply that there are no amino acid sequences from other sources. Other source amino acid sequences may, for example, comprise amino acid sequences from a recombinant organism. "Enriched" is meant to cover only those situations in which a person has intervened to elevate the proportion of the desired amino acid sequence.

The term "purified", in reference to a polypeptide, does not require absolute purity (such as a homogeneous preparation); instead, it represents an indication that the amino acid sequence is relatively more pure than in a cellular environment. The concentration of the preferred amino acid sequence should be at least 2–5 fold greater (in terms of mg/ml) than its concentration in a cellular environment. Purification of at least one order of magnitude, preferably two or three orders, and more preferably four or five orders of magnitude is preferred. The substance is preferably free of contamination, as indicated by purity levels of 90%, 95%, or 99%.

A preferred embodiment of the invention relates to a mCLK2, mCLK3, or mCLK4 polypeptide that is a unique fragment. This unique fragment can contain at least 17, 20, 25, 30, 35, 40, 50, 100, 200, 300, 400, 450, 475, or 485 contiguous amino acids of one of the full-length sequences. In addition, preferred lengths and portions of mCLK2, mCLK3, or mCLK4 amino acid sequences are encoded by the nucleic acid molecules defined in the first aspect of the invention.

The term "unique fragment" refers to the minimum stretch of amino acids in one mCLK molecule that is different in sequence than any other portion of another protein kinase. Since the largest identical stretch of amino acids found in FIG. 1, FIG. 2, FIG. 4, or FIG. 6 is seventeen amino acids, the minimum unique fragment for a mCLK protein kinase is seventeen amino acids.

The polypeptide can be isolated, enriched, or purified from a prokaryotic or eukaryotic recombinant cell. A eukaryotic cell includes mammals and preferably humans. Multiple standard techniques are available to those skilled in the art to facilitate isolation, enrichment, or purification of a polypeptide from recombinant cells. These methods typically include lysing the recombinant cells and separating the polypeptide of interest from the rest of the cell polypeptides, nucleic acids, and fatty acid-based material using standard chromatography techniques known in the art.

Another aspect of the invention features an antibody, that is monoclonal or polyclonal, or an antibody fragment having specific binding affinity to a mCLK2, mCLK3, or mCLK4 polypeptide.

Antibodies or antibody fragments are polypeptides with regions that can bind to other polypeptides with high affinity. The term "specific binding affinity" describes an antibody that binds to a mCLK2, mCLK3, or mCLK4 polypeptide with greater affinity than it binds to other polypeptides under specified conditions.

The term "polyclonal" refers to a mixture of antibodies with specific binding affinity to a mCLK2, mCLK3, or mCLK4 polypeptide, while the term "monoclonal" refers to one antibody with specific binding affinity to a mCLK2, mCLK3, or mCLK4 polypeptide. A monoclonal antibody binds to one specific region on a mCLK2, mCLK3, or mCLK4 polypeptide and a polyclonal mixture of antibodies can bind multiple regions of a mCLK2, mCLK3, or mCLK4 polypeptide. One skilled in the art would note that a monoclonal and especially a polyclonal antibody that has specific binding affinity to a mCLK2, mCLK3, or mCLK4 polypeptide will most likely also have specific binding affinity to another CLK protein kinase polypeptide of mammalian origin.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the ligand to which it binds specifically.

Antibodies or antibody fragments having specific binding affinity to a mCLK2, mCLK3, or mCLK4 polypeptide may be used in methods for detecting the presence and/or amount of a CLK protein kinase polypeptide in a sample by probing the sample with the antibody under conditions suitable for CLK protein kinase-antibody immunocomplex formation and detecting the presence and/or amount of the antibody conjugated to a CLK protein kinase polypeptide. Diagnostic kits for performing such methods may be constructed to include antibodies or antibody fragments specific for a CLK protein kinase as well as a conjugate of a binding partner of the antibodies or the antibodies themselves.

Another aspect of the invention features a hybridoma which produces an antibody having specific binding affinity to a mCLK2, mCLK3, or mCLK4 polypeptide. A "hybridoma" is an immortalized cell line which is capable of secreting an antibody, for example an antibody with specific binding affinity to a mCLK2, mCLK3, or mCLK4 polypeptide.

Another aspect of the invention relates to an isolated, enriched, or purified nucleic acid molecule comprising a nucleotide sequence that: (a) encodes a full length mCLK2, mCLK3, or mCLK4 amino acid sequence as set forth in FIG. 1, FIG. 2, FIG. 4, or FIG. 6; (b) encodes the complement of the nucleotide sequence encoding the amino acid sequences of FIG. 1, FIG. 2, FIG. 4, or FIG. 6; (c) hybridizes under highly stringent conditions to the nucleic acid molecule of (a) and encodes a naturally occurring mCLK2, mCLK3, or mCLK4 protein; (d) a mCLK2, mCLK3, or mCLK4 protein having the full length amino acid sequence as set forth in FIG. 1, FIG. 2, FIG. 4, or FIG. 6 except that it lacks one or more of the following segments of amino acid residues 1-182, 183-470, or 471499 of mCLK2, 1-176, 177-473, or 474-496 of mCLK3, or 1183, 184-486, or 486-489 of mCLK4; (e) the complement of the nucleotide sequence of (d); (f) a polypeptide having the amino acid sequence set forth in FIG. 1, FIG. 2, FIG. 4, or FIG. 6 from amino acid residues 1-182, 183-470, or 471-499 of mCLK2, 1176-, 177473, or 474-496 of mCLK3, or 1-183, 184-486, or 486-489 of mCLK4;(g) the complement of the nucleotide sequence of (f); (h) encodes a polypeptide having the full length amino acid sequence set forth in FIG. 1, FIG. 2, FIG. 4, or FIG. 6 except that it lacks one or more of the domains selected from the group consisting of a N-terminal domain, a catalytic domain, and a C-terminal-region; or (i) the complement of the nucleotide sequence of (h).

The term "N-terminal domain" refers to a portion of the full length mCLK2, mCLK3, or mCLK4 amino acid sequences spanning from the amino terminus to the start of the catalytic domain.

The term "catalytic domain" refers to a portion of the full length mCLK2, mCLK3, or mCLK4 amino acid molecules that does not contain the N-terminal domain or C-terminal region and has catalytic activity.

The term "C-terminal region" refers to a portion of the full length mCLK2, mCLK3, or mCLK4 amino acid molecules that begins at the end of the catalytic domain and ends at the carboxy terminal amino acid, which is the last amino acid encoded before the stop codon in the nucleic acid sequence.

Domains are regions of polypeptides which contain particular functions. For instance, N-terminal or C-terminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

Functional regions of mCLK2, mCLK3, or mCLK4 may be identified by aligning their amino acid sequences with amino acid sequences of other polypeptides with known functional regions. If regions of mCLK2, mCLK3, or mCLK4 share high amino acid identity with the amino acid sequences of known functional regions, then mCLK2, mCLK3, or mCLK4 can be determined to contain these functional regions by those skilled in the art. The functional regions can be determined, for example, by using computer programs and sequence information available to those skilled in the art.

Other functional regions of signal transduction molecules that may exist within mCLK2, mCLK3, or mCLK4 include, but are not limited to, proline-rich regions or phosphoryl tyrosine regions. These regions can interact with natural binding partners such as SH2 or SH3 domains of other signal transduction molecules. Another aspect of the invention relates to nucleic acid vectors comprising any of the nucleic acid molecules described herein.

In another aspect, the invention includes recombinant cells or tissues comprising any of the nucleic acid molecules described herein.

In yet another aspect, the invention relates to a method of identifying compounds capable of inhibiting or activating CLK protein kinase phosphorylation activity. This method comprises the following steps: (a) adding a compound to a mixture comprising a CLK protein kinase polypeptide and a substrate for a CLK protein kinase; and (b) detecting a change in phosphorylation of said substrate.

The term "compound" includes small organic molecules including, but not limited to, oxindolinones, quinazolines, tyrphostins, quinoxalines, and extracts from natural sources.

The term "CLK protein kinase polypeptide" refers to any CLK protein kinase isolated from an insect or a mammal. The polypeptide can be the full length amino acid sequence (the contiguous amino acids encoded by the nucleic acids spanning from the start codon to the stop codon of a naturally occurring CLK protein kinase nucleic acid molecule) or portions of a naturally occurring full length CLK protein kinase. Preferably, at least 17, 20, 25, 30, 35, 40, 50, 100, 200, 300, 400, 450, 475, or 485 contiguous amino acids are encoded for the CLK protein kinase polypeptide.

The term "a change in phosphorylation", in the context of the invention, defines a method of observing a change in phosphorylation of the substrate in response to adding a compound to cells. The phosphorylation can be detected, for example, by measuring the amount of a substrate that is converted to a product with respect to time. Addition of a compound to cells expressing a CLK protein kinase polypeptide may either enhance (activate) or lower (inhibit) the phosphorylation. If a compound lowers phosphorylation, the compound is assumed to bind to a CLK protein kinase polypeptide and block the ability of CLK protein kinase to bind and/or turn over a substrate. If a compound enhances phosphorylation, the compound is assumed to bind to a CLK protein kinase polypeptide and facilitate the ability of CLK protein kinase to bind and/or turn over a substrate.

The method can utilize any of the molecules disclosed in the invention. These molecules include nucleic acid molecules encoding mCLK2, mCLK3, or mCLK4 polypeptides, nucleic acid vectors, recombinant cells, polypeptides, or antibodies of the invention.

Another aspect of the invention is a method of identifying compounds useful for the diagnosis or treatment of an abnormal condition in an organism. The abnormal condition can be associated with an aberration in a signal transduction pathway characterized by an interaction between a CLK protein kinase polypeptide and a natural binding partner. The method comprises the following steps: (a) adding a compound to cells; and (b) detecting whether the compound promotes or disrupts said interaction between a CLK protein kinase polypeptide and a natural binding partner.

The term "abnormal condition" refers to a function in an organism's cells or tissue that deviate from a normal function in the cells or tissue of that organism. In the context of this aspect of the invention, abnormal conditions can be associated with cell proliferation or with RNA splicing.

Aberrant cell proliferative conditions include cancers such as fibrotic and mesangial disorders, abnormal angiogenesis and vasculogenesis, wound healing, psoriasis, diabetes mellitus, and inflammation.

RNA splicing is a necessary function of a cell that occurs in a cell nucleus. This process is the last step in the synthesis of message RNA from DNA. One molecule of RNA transcribed from DNA is tied into a lariat, incised in at least two places at the intersection of the strands, the lariat is excised, and the non-excised portion is ligated together. The modified RNA is then fit to be message RNA and is ejected from the cell nucleus to be translated into a polypeptide. Thus any aberrations that exist in an organisms ability to splice the RNA of a particular gene could result in the deficiency of a cellular agent and give rise to an abnormal condition.

Thus, regulating RNA splicing could be useful in treating cancer. For example, it is known that proteins such as Raf or src become oncogenic when made in a truncated form, such as could happen when RNA is incorrectly spliced. For this reason, the proteins of the invention might be useful for finding compounds to treat cancer. In addition, molecules involved in RNA processing have been linked to spermatogenesis. Thus, modifying RNA processing could lead to more sperm (to treat infertility) or less sperm. These methods would preferably involve CLK3 due to its high expression in the testis.

The abnormal condition can be diagnosed when the organism's cells exist within the organism or outside of the organism. Cells existing outside the organism can be maintained or grown in cell culture dishes. For cells harbored within the organism, many techniques exist in the art to administer compounds, including (but not limited to) oral, parenteral, dermal, and injection applications. For cells outside of the patient, multiple techniques exist in the art to administer the compounds, including (but not limited to) cell microinjection techniques, transformation techniques, and carrier techniques.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein kinases, receptor and non-receptor protein phosphatases, and transcription factors.

The term "aberration", in conjunction with a signal transduction process, refers to a CLK protein kinase polypeptide that is over- or under-expressed in an organism, mutated such that its catalytic activity is lower or higher than wild-type CLK protein kinase, mutated such that it can no longer interact with a binding partner, is no longer modified by another protein kinase or protein phosphatase, or no longer interacts with a binding partner.

The term "interaction" defines the complex formed between a CLK protein kinase polypeptide and a natural binding partner. Compounds can bind to either the CLK protein kinase polypeptide or the natural binding partner and disrupt the interaction between the two molecules. The method can also be performed by administering a group of cells containing an aberration in a signal transduction process to an organism and monitoring the effect of administering a compound on organism function. The art contains multiple methods of introducing a group of cells to an organism as well as methods of administering a compound to an organism. The organism is preferably an animal such as a frog, mouse, rat, rabbit, monkey, or ape, and also a human.

Methods of determining a compound's effect of detecting an interaction between CLK serine/threonine kinases and natural binding partners exist in the art. These methods include, but are not limited to, determining the effect of the compound upon the catalytic activity of a CLK protein kinase polypeptide, the phosphorylation state of the CLK protein kinase polypeptides or natural binding partners, the ability of a CLK protein kinase to bind a natural binding partner, or a difference in a cell morphology.

Differences in cell morphology include growth rates, differentiation rates, cell hypertrophy, survival, or prevention of cell death. These phenomena are simply measured by methods in the art. These methods can involve observing the number of cells or the appearance of cells under a microscope with respect to time (days).

Another aspect of the invention relates to a method of diagnosing an abnormal condition associated with cell proliferation or RNA splicing in an organism. The abnormal condition can be associated with an aberration in a signal transduction pathway characterized by an interaction between a CLK protein kinase polypeptide and a natural binding partner. The method comprises the step of detecting the abnormal interaction.

The abnormal interaction can be assessed by the methods described above in reference to the identification of compounds useful for diagnosing an abnormal condition in an organism.

In a final aspect, the invention features a method of administering a compound to a male organism that acts a contraceptive to reproduction. The compound can inhibit the catalytic activity of a CLK protein kinase or inhibit the binding of a natural binding partner to a CLK protein kinase.

Preferred embodiments of the methods of the invention relate to CLK serine/threonine kinases that are isolated from mammals, preferably humans, and to organisms that are mammals, preferably humans.

The summary of the invention described above is not limiting and other features and advantages of the invention will be apparent from the following detailed description of the invention, and from the claims.

BRIEF DESCRIPTION OF THE FIGURES

FIG. 1 compares amino acid sequences encoded by mCLK1, mCLK2, mCLK3, and mCLK4 nucleic acid molecules cloned from mouse cells. Each amino acid sequence is encoded between a start codon and a stop codon from its respective nucleic acid molecule. Dots indicate identical amino acids and hyphens are introduced for optimal alignment. The predicted nuclear localization signals are underlined. Invariant amino acids signifying CDC2 like kinases are printed in bold. The catalytic domain is indicated by arrows. The LAMMER signature is indicated by asterisks.

FIG. 2 depicts an amino acid sequence of mCLK2 (SEQ ID NO:21).

FIG. 3 depicts a nucleic acid sequence of mCLK2 (SEQ ID NO:22).

FIG. 4 depicts an amino acid sequence of mCLK3 (SEQ ID NO:23).

FIG. 5 depicts a nucleic acid sequence of mCLK3 (SEQ ID NO:24).

FIG. 6 depicts an amino acid sequence of mCLK4 (SEQ ID NO:25).

FIG. 7 depicts a nucleic acid sequence of mCLK4 (SEQ ID NO:26).

DETAILED DESCRIPTION OF THE INVENTION

The present invention is based in part upon the isolation and characterization of nucleic acid molecules encoding novel protein kinases designated mCLK2, mCLK3, and mCLK4. The invention also relates to nucleic acid molecules encoding portions of these protein kinase polypeptides, nucleic acid molecules encoding at least one mCLK2, mCLK3, or mCLK4 functional region, nucleic acid vectors harboring such nucleic acid molecules, cells containing such nucleic acid vectors, purified polypeptides encoded by such nucleic acid molecules, antibodies to such polypeptides, and methods of identifying compounds that bind CLK serine/threonine kinases or abrogate their interactions with natural binding partners. Also disclosed are methods for diagnosing abnormal conditions in an organism with CLK protein kinase related molecules or compounds. The invention also concerns using a CLK protein kinase related molecule or compound as a contraceptive to reproduction in a male organism.

The present invention discloses the discovery of the protein kinases, mCLK2, mCLK3, and mCLK4. The predicted molecular weights of the encoded proteins are 59.9 kDa (mCLK2), 58.5 kDa (mCLK3), and 57.2 kDa (mCLK4).

As illustrated in FIG. 1, mCLK1, mCLK2, mCLK3, and mCLK4 share the essential features identifying them as LAMMER kinases. Yun et al., 1994, *Genes. Dev.* 8:1160–1173. They contain a nuclear localization signal (Dingwall and Laskey, 1991, *Trends Biochem. Sci.* 16:478–481), as well as an unusually basic amino terminus composed of many serine and arginine residues. These serine and arginine amino acids likely embody a signal sequence localizing the protein to nuclear speckles. Hedley et al., 1995, *Proc. Natl. Acad. Sci. USA* 92:11524–11528; Colwill et al., 1996, *EMBO J.* 15:265–275. The amino terminus is the most divergent portion of the proteins, suggesting that this area could contain information specific to each protein. The catalytic domain is homologous among all family members, with only few amino acid changes. Furthermore, all amino acids known to define the subfamily of CDC2 like kinases are present in all four proteins. Ben-David et al., 1991, *EMBO J.* 10:317–325.

mCLK1 has been shown to interact with ASF/SF2, SRp20 and hnRNP proteins in a yeast two hybrid system. Because hnRNP-K binds to the protooncogene $p95^{vav}$, mCLK1 could be implicated in transmitting signals that regulate the expression of the protooncogenes myc and fos in hematopoietic cells. Thus the role of CLK serine/threonine kinases may not be limited to simply maintaining RNA splicing and translocation events in the cell; CLK serine/threonine kinases may also be linked to regulating the flow of extracellular signals within hematopoietic cells. In addition, CLK serine/threonine kinases may be targets for compounds that could ameliorate cancers associated with uncontrolled regulation of the protooncogenes $p_{95}^{vav}$, myc, and fos. Because over-expression of CLK seriSe/threonine kinases themselves have been implicated in certain types of cancer cell lines, compounds that inhibit their catalytic activity or disrupt their interactions with natural binding partners may act as anti-cancer therapeutics.

Even though CLK serine/threonine kinases other than mCLK2, mCLK3, and mCLK4 have been described previously, the methods of the invention relate to CLK serine/threonine kinases in general as the methods described herein are not disclosed elsewhere. Thus the methods of the invention include antibodies and other compounds with specific binding affinity to mCLK2, mCLK3, and mCLK4 as well as antibodies and other compounds that interact with other CLK protein kinase polypeptides.

Various other features and aspects of the invention are: nucleic acid molecules encoding a mCLK2, mCLK3, or mCLK4 polypeptide; nucleic acid probes for the detection of CLK serine/threonine kinases; a probe-based method and kit for detecting CLK protein kinase messages in other organisms; DNA constructs comprising a mCLK2, mCLK3, or mCLK4 nucleic acid molecule and cells containing these constructs; purified mCLK2, mCLK3, or mCLK4 polypeptides; mCLK2, mCLK3, or mCLK4 antibodies and hybridomas; antibody-based methods and kits for detecting CLK serine/threonine kinases; identification of agents; isolation of compounds which interact with a CLK protein kinase polypeptide; compositions of compounds that interact with CLK serine/threonine kinases; pharmaceutical formulations and modes of administration; derivatives of complexes; antibodies to complexes; disruption of CLK protein kinase protein complexes; purification and production of complexes; transgenic animals containing mCLK2, mCLK3, or mCLK4 nucleic acid constructs; antisense and ribozyme approaches, gene therapy; and evaluation of disorders. One skilled in the art would note that a derivative of a complex can manifest itself as a derivative of any one of the molecules in that complex, including derivatives of a nucleic acid molecule, a polypeptide, or a compound bound to a polypeptide. All of these aspects and features are explained in detail with respect to the protein PYK-2 in PCT publication WO 96/18738, which is incorporated herein by reference in its entirety, including any drawings. Those skilled in the art will readily appreciate that such descriptions can be easily adapted to mCLK2, mCLK3, mCLK4, or other CLK serine/threonine kinases as well, and is equally applicable to the present invention.

Other features and aspects of the invention are depicted in PCT Application WO 97/48723 (PCT/IB97/00946), published on Dec. 24, 1997, filed on Jun. 17, 1997, Axel Ullrich et al., entitled "Novel PTP20, PCP-2, BDP-1, CLK, and SIRP Proteins and Related Products and Methods," hereby incoroporated by reference herein in its entirety, including all figures, tables, and drawings.

EXAMPLES

The examples below are non-limiting and are merely representative of various aspects and features of the present invention. The examples below demonstrate the isolation, and characterization of the novel protein kinases, mCLK2, mCLK3, and mCLK4.

Example 1

PCR Amplification and Cloning

The catalytic domain of protein kinases contains highly conserved regions, which have been successfully used to PCR amplify and clone novel family members from a variety of species and tissues. The signature sequence HRDLAAR in the catalytic subdomain VI and D(V/M)WS(Y/F)G in subdomain IX were used to create degenerate oligonucleotides. Ciossek et al., 1995, *Oncogene* 11:2085–2095. These primers were then used to search for unknown protein kinases involved in muscle cell differentiation using reverse transcriptase PCR of total RNA, isolated from various in vitro differentiated stages of the mouse myoblast cell line C2C12. Lechner et al., 1996, *Proc. Natl. Acad. Sci. USA* 93:4355–4359.

From the approximately 300 fragments which were sequenced one was novel. It derived from a member of the LAMMER family of dual specificity kinases (Yun et al., 1994, *Genes. Dev.* 8:1160–1173), also known as CLK kinases (Ben-David et al., 1991, *EMBO J.* 10:317–325) or STY (Howell et al., 1991, *Mol. Cell. Biol.* 11:568–572) and shared a high homology to a part of the human cDNA hCLK2. To obtain the full length clone and to search for other closely related sequences, a mouse 11.5 p.c. embryonic library was screened at low stringency using the original 250 bp PCR fragment as a probe. Three highly related full-length cDNA sequences defining different members of the CLK family using this technique.

The same libraries were rescreened with a mixture of mCLK1, 2, 3, and 4 fragments at low stringency to isolate additional novel members of this family. Reverse transcriptase PCR reactions were performed on brain, kidney and liver poly (A)+ RNA with degenerate primers coding for the DLKPEN (SEQ ID NO. 1) and AMMERI (SEQ ID NO. 2) motifs. These efforts did not identify additional genes.

Reverse transcriptase PCR reactions were performed with 2 µg of total RNA prepared from confluent or differentiated (day 7) mouse C2C12 myoblasts (Lechner et al., 1996, *Proc. Natl. Acad. Sci. USA* 93:4355–4359) using degenerate oligonucleotide primers. Ciossek et al., 1995, *Oncogene* 11:2085–2095. Briefly, 2 µg of RNA were reverse transcribed in the presence of 1 µM degenerate antisense primer, 250 µM of each nucleotide and 75 units of Stratascript reverse transcriptase (Stratagene) in a total volume of 20 µl for 30 min at 42° C. 2 µl of the above reaction was used in a PCR reaction using degenerate sense and antisense oligonucleotides (1 µM each), 25 µM of each nucleotide and 2.5 units Taq polymerase (Boehringer). 30 cycles were performed with 1 min for each 94° C., 50° C. and 72° C. step. Fragments of approximately 250 bp were gel purified, cloned in Bluescript and sequenced.

mCLK2, mCLK3 and mCLK4 were cloned from a mouse embryo 11.5 p.c. 1ZAP cDNA library (Ciossek et al., 1995, Oncogene 11:2085–2095) using the isolated PCR fragment as a probe according to manufacturer's instructions (final wash in 0.5× SSC/0.1%SDS at 42° C.) (Stratagene). mCLK1 was cloned by reverse transcriptase PCR from lug brain poly (A)+ RNA using specific primers mCLK1s-Bam, CGG-GATCCCTTCGCCTTGCAGCTTTGTC (SEQ ID NO. 3) and mCLK1as-EcoRI, CGGAATTCCTAGACTGATA-CAGTCTGTAAG (SEQ ID NO. 4), and Pwo polymerase (Boehringer).

DNA sequencing was performed using the dideoxynucleotide chain termination method (Sanger et al., 1977, *Proc. Natl. Acad. Sci. USA* 74:5463–5467) using sequenase, reagents and protocols supplied by United States Biochemical Corporation. Comparisons of the deduced protein sequences were carried out using MacDNASIS PRO (Hitachi) software. Amino acid alignments were constructed using a Waterman algorithm.

Example 2

Tissue Distribution of CLK Serine/Threonine Kinases

Expression patterns of CLK kinase genes (including the previously cloned mCLK1) were analyzed by Northern blot hybridization of total RNA from selected mouse tissues, as well as from different mouse tumor cell lines. Each CLK gene was detected in all investigated tissues, although the expression patterns were different for each gene. The expected size of the full-length mRNA is ~1.8 kb for all CLK kinases, and this was detected in all tissues and cell lines, albeit at different levels.

A doublet was detected at around 1.8 kb, whereby the upper band represents the message of the full length protein and the lower one is likely to be the alternatively spliced form, responsible for a truncated, catalytically inactive protein. Duncan et al., 1995, *J. Biol. Chem.* 270:21524–21531. Commensurate with this alternative splice, differences in the ratio of the two alternatively spliced messages were detected for each CLK gene.

Differences in expression patterns were observed for the CLK genes, especially in testes. Low mCLK1 expression levels were observed in testes as compared to mCLK2, mCLK3 and mCLK4. However, while almost all of the mCLK3 message represented the catalytically active splice form, mCLK4 was expressed predominantly as a message encoding the truncated protein. mCLK2 was also highly expressed in this tissue, but as a larger transcript. Similar large transcripts, which did not correspond to the expected message size, were detected for all mCLK genes which most likely represented non- or partially spliced messages in analogy to mCLK1. Duncan et al., 1995, *J. Biol. Chem.* 270:21524–21531. The ratio of these larger RNA species, when compared to the coding mRNA, varied among the CLK kinases.

Because it was reported (Ben-David et al., 1991, *EMBO J.* 10:317–325) that mCLK1 kinase was over-expressed in certain cancer cell lines, studies were extended to mCLK1-4. Although messages for the four genes were detected in all cell lines tested, albeit in sometimes very low quantities, significant differences of expression levels between the cell lines for each individual gene were observed. However, an overall increase of mCLK mRNA was not detected in transformed cells, even though higher levels of particular mCLK messages were detected in some cell. Low expression levels were detected in Hybridoma, WEHI and NF561 cell lines, with the majority of the messages representing the splice form encoding the truncated product. The mRNA expression levels of mCLK1-4 genes were investigated in the C2C12 cell line and Li adipocytes during differentiation, but no noticeable change in expression was detected.

RNA was extracted from frozen adult mice tissues or tissue culture cells. Puissant and Houdebine, 1990, *Biotechniques* 8:148–149. 10 µg total RNA was then electrophoresed in 1.2% agarose formaldehyde gels (Sambrook et al., 1989, *Cold Spring Harbour Laboratory Press*) and transferred to Hybond N membranes (Amersham). Hybridization was performed overnight in 50% formamide, 5× SSC (750 mM sodium chloride, 75 mM sodium citrate), 5× Denhardt's (0.1% Ficoll 400, 0.1% polyvinylpyrrolidone, 0.1%BSA), 0.2% SDS and 100 µg/ml salmon sperm DNA. 1-3×10$^6$ cpM/ml of $^{32}$P-random primed DNA probe (Amersham Megaprime kit) was used, followed by washes at 0.2× SSC/0.1%SDS at 42° C. Blots were incubated with Hyperfilm-MP (Amersham) at -80° C. for 2 weeks. Membranes were stripped for reuse by boiling in 0.1% SDS/water.

Example 3

Expression of Functionally Active CLK Protein Kinases

Glutathione S-transferase (GST) mCLK1-4 fusion constructs were generated to investigate the catalytic activity of these protein kinases. These protein kinases were cloned from pcDNA and expressed in vitro. The expression levels were almost identical and full-length fusion proteins of the expected molecular weights were obtained. The GST fusion proteins were purified on glutathione-sepharose beads and utilized to perform in vitro kinase assays using myelin basic protein or histone H1 as substrates. All constructs were catalytically active, autophosphorylated, and the levels of activity were clearly above the background seen from an equivalent amount of in vitro produced GST protein alone.

Catalytically inactive lysine to arginine mutants could not phosphorylate any substrate above background phosphorylation. However, mCLK1 and mCLK4 displayed a dramatic difference in enzymatic activity versus mCLK2 and mCLK3. This observation was consistent even when changing a variety of buffer conditions during fusion protein purification and assays or when changing metal ion concentrations. Several fold changes in kinase activity were observed due to the conditions used, but differences in enzymatic activities seen between the two groups of mCLK kinases persisted.

Phosphorylation specificity of mCLK1-4 protein kinases were examined and compared using biochemically purified and dephosphorylated SR proteins as substrates. SR proteins were purified from $5 \times 10^9$ log phase F-MEL suspension cells according to standard procedures. An aliquot of the purified proteins was analyzed by sodium dodecyl sulfate polyacrylamide gel electrophoresis (SDS-PAGE) to confirm that the expected proteins were purified to near homogeneity.

Following dephosphorylation by the protein phosphatase 1g catalytic subunit, SR proteins were used as substrates for the in vitro produced and purified GSTmCLK1-4 fusion proteins in an in vitro kinase assay. All mCLK kinases were able to phosphorylate SRp20, SRp30a and to a lesser extent SRp40 and SRp55. The lower signal of SRp40 and SRp55 relative to SRp20 and SRp30 most likely reflected the lower quantity of these proteins. SRp75 was not visualized in these experiments since the autophosphorylated mCLK proteins migrated at the same position. mCLK1 and mCLK4 phosphorylated SRp30a (upper band) more strongly than SRp30b, whereas mCLK2 and mCLK3 phosphorylated both with almost equal efficiency. A marked difference in catalytic activity was visualized between mCLK1 and mCLK4 versus mCLK2 and mCLK3, despite equal amounts of protein in each assay.

To investigate the specificity of mCLK kinases, recombinant human peptidyl-prolyl isomerase PIN1 was utilized as a substrate. Lu et al., 1996, *Nature* 380:544–547. Although it also contains several amino terminal serine and arginine residues and is localized to nuclear speckles, neither of the mCLK kinases was able to phosphorylate this protein in vitro.

GST fusion constructs were generated by subcloning full length mCLK1, mCLK2, mCLK3 and mCLK4 cDNAs by PCR into pGEX vectors (Pharmacia), creating in-frame glutathione S-transferase (GST) fusion constructs using the following primers for PCR: mCLK1s-Bam (as above);

```
mCLK1as-Not I,    TATAGCGGCCGCTAGACTGATACAGTCTGT              (SEQ ID NO. 5);

mCLK2s-Sma I,     TCCCCCGGGATGCCCCATCCCCGAAGGTACCA            (SEQ ID NO. 6);

mCLK2as-Not I,    TATAGCGGCCGCTCACCGACTGATATCCCGACTGGAGTC     (SEQ ID NO. 7);

mCLK3s-Sma I,     TCCCCCGGGGAGACGATGCATCACTGTAAG              (SEQ ID NO. 8);

mCLK3as-Not I,    TATAGCGGCCGCGCTGGCCTGCACCTGTCATCTGCTGGG     (SEQ ID NO. 9);

mCLK4s-EcoRI,     CGGAATTCATGCGGCATTCCAAACGAACTC              (SEQ ID NO. 10), mCLK4as-Not I,    TATAGCGGCCGCCCTGACTCCCACTCATTTCCTTTTTAA     (SEQ ID NO. 11).

The cDNAs encoding the fusion construct were then recloned
in pcDNA3 (Invitrogen) by PCR using the GST upstream primers:

GST-EcoRI,        CGGAATTCCGCCACCATGGCCCCTATACTAGGTTAT        (SEQ ID NO. 12)
                                                              (for mCLK1) and
GST-Hind III,     GCCAAGCTTGCCACCATGGCCCCTATACTAGGTTAT        (SEQ ID NO. 13)
                                                              (for mCLK2,
                                                              mCLK3 and
                                                              mCLK4).
```

Integrity of the clones was checked by sequencing and by a coupled transcription-translation assay using T7 RNA polymerase and rabbit reticulocyte lysate according to the manufacturer's protocol (Promega).

mCLK 1-4 mutants containing a lysine (K) to arginine (R) substitution at position 190 (mCLK1), 192 (mCLK2), 186 (mCLK3) and 189 (mCLK4) were generated using a site-directed mutagenesis protocol. Kunkel, 1985, *Proc. Natl. Acad. Sci. USA* 82:488–492. Oligonucleotide primers were as follows:

```
(mCLK1-K190R)  GTAGCAGTAAGAATAGTTAAA;

(mCLK2-K192R)  (SEQ ID NO. 14)  GTTGCCCTGAGGATCATTAAGAAT;

(mCLK3-K186R)  (SEQ ID NO. 15)  GTTGCCCTGAGGATCATCCGGAAT;

(mCLK4-K189R)  (SEQ ID NO. 16)  TACAATTCTCACTGCTACATGTAAGCCATC (SEQ ID NO. 17)
```

$^{35}$S-methionine labeled GST-mCLK1-4 fusion proteins were produced in a 50 gl coupled in vitro transcription/translation reaction using manufacturer's instructions (Promega).

2 gl of each lysate was checked and quantified for the amounts of produced protein by SDS-PAGE and autoradiography. Equal amounts (usually 20–30 µl of lysate) were added to 500 µl PBS (1 mM PMSF, 10 µg/ml aprotinine), 30 µl of GSH-sepharose beads (Pharmacia) and incubated on a rotating wheel for 2 hours at 4° C. This step resulted in quantitative binding of the fusion proteins. The beads were then washed three times in 500 µl PBS and once in 500 µl kinase assay buffer (20 mM Hepes, 10M MgCl$_2$, 1 mM DTT, 200 µM sodium orthovanadate, 1 mM EGTA, pH 7.5). The assay was carried out for 30 minutes at room temperature in 30 µl kinase assay buffer with 20 µM ATP, 4 µCi γ-$^{32}$P-ATP (Amersham, 10 mCi/ml) and 14.5 µg of myelin basic protein (Sigma) or histone H1 (Boehringer) respectively.

SR protein kinase assays were essentially carried out as described above, except that ~2.5 µg of dephosphorylated SR proteins were used and that the kinase assay buffer also contained 1 µM Microcystin LR (Sigma). The reaction was stopped by adding 30 µl of 2× SDS sample buffer. The samples were boiled for 5 minutes and 15 µl were loaded on a 15% SDS-polyacrylamide gel. Following electrophoresis, the gels were stained with Coomassie, dried and exposed to Hyperfilm-MP (Amersham) for 24 hours. The $^{35}$S-methionine signal was suppressed with a 3M Whatman paper placed between the film and the gel.

SR proteins were purified from 5×10$^9$ Friend murine erythroleukemia cells (F-MEL) according to the protocol described (Zahler et al., 1992, *Genes Dev* 6:837–847) and resuspended in buffer D. Dignam et al., 1983, *Nucleic Acids Res.* 11:1475–1489. 30 µl of SR proteins (~0.5 µg/µl) were incubated on ice for 10 minutes in 0.7 mM MnCl$_2$ and 5 mU Protein Phosphatase 1g-catalytic subunit (Boehringer), followed by 60 minutes at 30° C. Mermoud et al., 1994, *EMBO J.* 13:5679–5688. 5 µl of dephosphorylated SR proteins were used per assay.

Example 4

Nucleic Acid Probes, Methods, and Kits For Detection of CLK Kinases and Other Related Polypeptides A nucleic acid probe of the present invention may be used to probe an appropriate chromosomal or cDNA library by usual hybridization methods to obtain other nucleic acid molecules of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis can be carried out in order to obtain nucleic acid probes having nucleotide sequences which correspond to N-terminal and Cterminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael, et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

One method of detecting the presence of nucleic acids of the invention in a sample comprises (a) contacting said sample with the above-described nucleic acid probe under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of nucleic acids of the invention in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or streptavidin). Preferably, the kit further comprises instructions for use.

A compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers include a container that accepts the test sample, a container that contains the probe or primers used in the assay, containers that contain wash reagents (such as phosphate buffered saline, Tris-buffers, and the like), and containers that contain the reagents used to detect the hybridized probe, bound antibody, amplified product, or the like. One skilled in the art will readily recognize that the nucleic acid probes described in the present invention can readily be incorporated into one of the established kit formats that are well known in the art.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In particular, although some formulations described herein have been identified by the excipients added to the formulations, the invention is meant to also cover the final formulation formed by the combination of these excipients. Specifically, the invention includes formulations in which one to all of the added excipients undergo a reaction during formulation and are no longer present in the final formulation, or are present in modified forms.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are encompassed by the following claims.

35

What is claimed is:
1. An isolated, enriched, or purified nucleic acid molecule comprising a nucleotide sequence that:
 (a) encodes a polypeptide having the full length amino acid sequence set forth in SEQ ID NO: 21;
 (b) is the complement of the nucleotide sequence of (a);
 (c) differs from the nucleic acid sequence encoding SEQ ID NO:21 by lacking one of the following segments of amino acid residues: 1-182, 183-470, or 471-499;
 (d) is the complement of the nucleotide sequence of (c);
 (e) encodes a polypeptide having the amino acid sequence set forth in residues 1-182 or encodes a polypeptide consisting of the amino acid sequence set forth in residues 471-499 of SEQ ID NO:21;
 (f) is the complement of the nucleotide sequence of (e);
 (g) has the full length nucleotide sequence set forth in SEQ ID NO:22; or
 (h) is the complement of the nucleotide sequence of(g).
2. The isolated acid molecule of claim 1, wherein said nucleic acid molecule is obtained from a mammal.
3. The nucleic acid according to claim 1, wherein said nucleic acid is isolated from blood, semen or tissue.

4. An insolated or purified nucleic acid said vector comprising (i) a nucleic acid molecule according to claim 1, and (ii) a promoter element,
 wherein said nucleic acid molecule and said promoter element are incorporated into said nucleic acid vector so that said promoter element is effective to initiate transcription of said nucleic acid molecule in a cell.
5. A recombinant cell comprising the nucleic acid molecule according to claim 1.
6. A recombinant cell comprising the vector according to claim 4.
7. An isolated or purified nucleic acid vector comprising (i) a nucleic acid molecule encoding a polypeptide having the amino acid sequence set forth in SEQ ID NO: 21 and (ii) a promoter element,
 wherein said nucleic acid molecule and said promoter element are incorporated into said nucleic acid vector so that said promoter element is effective to initiate transcription of said nucleic acid molecule in a cell.
8. A recombinant cell comprising the vector according to claim 7.

* * * * *

UNITED STATES PATENT AND TRADEMARK OFFICE
CERTIFICATE OF CORRECTION

PATENT NO. : 6,797,513 B2
DATED : September 28, 2004
INVENTOR(S) : Axel Ullrich et al.

It is certified that error appears in the above-identified patent and that said Letters Patent is hereby corrected as shown below:

Title page,
Item [*] Notice, should read -- 176 days instead of 53 days --.

Signed and Sealed this

Fourteenth Day of March, 2006

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 6
<212> TYPE: PRT
<213> ORGANISM: Mus musculus

<400> SEQUENCE: 1

Asp Leu Lys Pro Glu Asn
1               5

<210> SEQ ID NO 2
<211> LENGTH: 6
<212> TYPE: PRT
<213> ORGANISM: Mus musculus

<400> SEQUENCE: 2

Ala Met Met Glu Arg Ile
1               5

<210> SEQ ID NO 3
<211> LENGTH: 28
<212> TYPE: DNA
<213> ORGANISM: Mus musculus

<400> SEQUENCE: 3
cgggatccct tcgccttgca gctttgtc                                      28

<210> SEQ ID NO 4
<211> LENGTH: 30
<212> TYPE: DNA
<213> ORGANISM: Mus musculus

<400> SEQUENCE: 4
cggaattcct agactgatac agtctgtaag                                    30

<210> SEQ ID NO 5
<211> LENGTH: 30
<212> TYPE: DNA
<213> ORGANISM: Mus musculus

<400> SEQUENCE: 5
tatagcggcc gctagactga tacagtctgt                                    30
```

<210> SEQ ID NO 6
<211> LENGTH: 32
<212> TYPE: DNA
<213> ORGANISM: Mus musculus

<400> SEQUENCE: 6
tcccccggga tgccccatcc ccgaaggtac ca                          32

<210> SEQ ID NO 7
<211> LENGTH: 39
<212> TYPE: DNA
<213> ORGANISM: Mus musculus

<400> SEQUENCE: 7
tatagcggcc gctcaccgac tgatatcccg actggagtc                   39

<210> SEQ ID NO 8
<211> LENGTH: 30
<212> TYPE: DNA
<213> ORGANISM: Mus musculus

<400> SEQUENCE: 8
tcccccgggg agacgatgca tcactgtaag                             30

<210> SEQ ID NO 9
<211> LENGTH: 39
<212> TYPE: DNA
<213> ORGANISM: Mus musculus

<400> SEQUENCE: 9
tatagcggcc gcgctggcct gcacctgtca tctgctggg                   39

<210> SEQ ID NO 10
<211> LENGTH: 30
<212> TYPE: DNA
<213> ORGANISM: Mus musculus

<400> SEQUENCE: 10
cggaattcat gcggcattcc aaacgaactc                             30

<210> SEQ ID NO 11
<211> LENGTH: 39
<212> TYPE: DNA
<213> ORGANISM: Mus musculus

<400> SEQUENCE: 11
tatagcggcc gccctgactc ccactcattt cctttttaa                   39

<210> SEQ ID NO 12
<211> LENGTH: 36
<212> TYPE: DNA
<213> ORGANISM: Mus musculus

<400> SEQUENCE: 12
cggaattccg ccaccatggc ccctatacta ggttat                      36

<210> SEQ ID NO 13
<211> LENGTH: 36
<212> TYPE: DNA
<213> ORGANISM: Mus musculus

<400> SEQUENCE: 13

-continued gccaagcttg ccaccatggc ccctatacta ggttat         36

<210> SEQ ID NO 14
<211> LENGTH: 21
<212> TYPE: DNA
<213> ORGANISM: Mus musculus

<400> SEQUENCE: 14
gtagcagtaa gaatagttaa a         21

<210> SEQ ID NO 15
<211> LENGTH: 24
<212> TYPE: DNA
<213> ORGANISM: Mus musculus

<400> SEQUENCE: 15
gttgccctga ggatcattaa gaat         24

<210> SEQ ID NO 16
<211> LENGTH: 24
<212> TYPE: DNA
<213> ORGANISM: Mus musculus

<400> SEQUENCE: 16
gttgccctga ggatcatccg gaat         24

<210> SEQ ID NO 17
<211> LENGTH: 30
<212> TYPE: DNA
<213> ORGANISM: Mus musculus

<400> SEQUENCE: 17
tacaattctc actgctacat gtaagccatc         30

<210> SEQ ID NO 18
<211> LENGTH: 7
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesized protein kinase

<400> SEQUENCE: 18

His Arg Asp Leu Ala Ala Arg
1               5

<210> SEQ ID NO 19
<211> LENGTH: 6
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthesized protein kinase
<221> NAME/KEY: misc_feature
<222> LOCATION: (2)..(2)
<223> OTHER INFORMATION: Xaa at position 2 can be Val or Met
<221> NAME/KEY: misc_feature
<222> LOCATION: (5)..(5)
<223> OTHER INFORMATION: Xaa at position 5 can be Tyr or Phe

<400> SEQUENCE: 19

Asp Xaa Trp Ser Xaa Gly
1               5

<210> SEQ ID NO 20
<211> LENGTH: 483
<212> TYPE: PRT
<213> ORGANISM: Mus musculus

<400> SEQUENCE: 20

Met Arg His Ser Lys Arg Thr Tyr Cys Pro Asp Trp Asp Glu Arg Asp
1               5                   10                  15

Trp Asp Tyr Gly Thr Trp Arg Ser Ser Ser His Lys Arg Lys Lys
            20                  25                  30

Arg Ser His Ser Ser Ala Arg Glu Gln Lys Arg Cys Arg Tyr Asp His
        35                  40                  45

Ser Lys Thr Thr Asp Ser Tyr Tyr Leu Glu Ser Arg Ser Ile Asn Glu
    50                  55                  60

Lys Ala Tyr His Ser Arg Arg Tyr Val Asp Glu Tyr Arg Asn Asp Tyr
65                  70                  75                  80

Met Gly Tyr Glu Pro Gly His Pro Tyr Gly Glu Pro Gly Ser Arg Tyr
                85                  90                  95

Gln Met His Ser Ser Lys Ser Ser Gly Arg Ser Gly Arg Ser Ser Tyr
            100                 105                 110

Lys Ser Lys His Arg Ser Arg His His Thr Ser Gln His His Ser His
        115                 120                 125

Gly Lys Ser His Arg Arg Lys Arg Ser Arg Ser Val Glu Asp Asp Glu
    130                 135                 140

Glu Gly His Leu Ile Cys Gln Ser Gly Asp Val Leu Ser Ala Arg Tyr
145                 150                 155                 160

Glu Ile Val Asp Thr Leu Gly Glu Gly Ala Phe Gly Lys Val Val Glu
                165                 170                 175

Cys Ile Asp His Lys Val Gly Gly Arg Arg Val Ala Val Lys Ile Val
            180                 185                 190

Lys Asn Val Asp Arg Tyr Cys Glu Ala Ala Gln Ser Glu Ile Gln Val
        195                 200                 205

Leu Glu His Leu Asn Thr Thr Asp Pro His Ser Thr Phe Arg Cys Val
    210                 215                 220

Gln Met Leu Glu Trp Phe Glu His Arg Gly His Ile Cys Ile Val Phe
225                 230                 235                 240

Glu Leu Leu Gly Leu Ser Thr Tyr Asp Phe Ile Lys Glu Asn Ser Phe
                245                 250                 255

Leu Pro Phe Arg Met Asp His Ile Arg Lys Met Ala Tyr Gln Ile Cys
            260                 265                 270

Lys Ser Val Asn Phe Leu His Ser Met Lys Leu Thr His Thr Asp Leu
        275                 280                 285

Lys Pro Glu Asn Ile Leu Phe Val Lys Ser Asp Tyr Thr Glu Ala Tyr
    290                 295                 300

Asn Pro Lys Met Lys Arg Asp Glu Arg Thr Ile Val Asn Pro Asp Ile
305                 310                 315                 320

Lys Val Val Asp Phe Gly Ser Ala Thr Tyr Asp Asp Glu His His Ser
                325                 330                 335

Thr Leu Val Ser Thr Arg His Tyr Arg Ala Pro Glu Val Ile Leu Ala
            340                 345                 350

Leu Gly Trp Ser Gln Pro Cys Asp Val Trp Ser Ile Gly Cys Ile Leu
        355                 360                 365

Ile Glu Tyr Tyr Leu Gly Phe Thr Val Phe Pro Thr His Asp Ser Arg
    370                 375                 380

-continued

```
Glu His Leu Ala Met Met Glu Arg Ile Leu Gly Pro Leu Pro Lys His
385                 390                 395                 400

Met Ile Gln Lys Thr Arg Lys Arg Arg Tyr Phe His Asp Arg Leu
            405                 410                 415

Asp Trp Asp Glu His Ser Ser Ala Gly Arg Tyr Val Ser Arg Arg Cys
            420                 425                 430

Lys Pro Leu Lys Glu Phe Met Leu Ser Gln Asp Ala Glu His Glu Phe
            435                 440                 445

Leu Phe Asp Leu Val Gly Lys Ile Leu Glu Tyr Asp Pro Ala Lys Arg
            450                 455                 460

Ile Thr Leu Lys Glu Ala Leu Lys His Pro Phe Phe Tyr Pro Leu Lys
465                 470                 475                 480

Lys His Thr

<210> SEQ ID NO 21
<211> LENGTH: 499
<212> TYPE: PRT
<213> ORGANISM: Mus musculus

<400> SEQUENCE: 21

Met Pro His Pro Arg Arg Tyr His Ser Ser Glu Arg Gly Ser Arg Gly
1               5                   10                  15

Ser Tyr His Glu His Tyr Gln Ser Arg Lys His Lys Arg Arg Arg Ser
            20                  25                  30

Arg Ser Trp Ser Ser Ser Ser Asp Arg Thr Arg Arg Arg Arg Arg Glu
        35                  40                  45

Asp Ser Tyr His Val Arg Ser Arg Ser Tyr Asp Asp His Ser Ser
    50                  55                  60

Asp Arg Arg Leu Tyr Asp Arg Arg Tyr Cys Gly Ser Tyr Arg Arg Asn
65                  70                  75                  80

Asp Tyr Ser Arg Asp Arg Gly Glu Ala Tyr Tyr Asp Thr Asp Phe Arg
                85                  90                  95

Gln Ser Tyr Glu Tyr His Arg Glu Asn Ser Ser Tyr Arg Ser Gln Arg
            100                 105                 110

Ser Ser Arg Arg Lys His Arg Arg Arg Arg Arg Ser Arg Thr Phe
        115                 120                 125

Ser Arg Ser Ser Ser His Ser Ser Arg Arg Ala Lys Ser Val Glu Asp
    130                 135                 140

Asp Ala Glu Gly His Leu Ile Tyr His Val Gly Asp Trp Leu Gln Glu
145                 150                 155                 160

Arg Tyr Glu Ile Val Ser Thr Leu Gly Glu Gly Thr Ser Gly Arg Val
                165                 170                 175

Val Gln Cys Val Asp His Arg Arg Gly Gly Thr Arg Val Ala Leu Lys
            180                 185                 190

Ile Ile Lys Asn Val Glu Lys Tyr Lys Glu Ala Ala Arg Leu Glu Ile
        195                 200                 205

Asn Val Leu Glu Lys Ile Asn Glu Lys Asp Pro Asp Asn Lys Asn Leu
    210                 215                 220

Cys Val Gln Met Phe Asp Trp Phe Asp Tyr His Gly His Met Cys Ile
225                 230                 235                 240

Ser Phe Glu Leu Leu Gly Leu Ser Thr Phe Asp Phe Leu Lys Asp Asn
                245                 250                 255

Asn Tyr Leu Pro Tyr Pro Ile His Gln Val Arg His Met Ala Phe Gln
            260                 265                 270
```

```
Leu Cys Gln Ala Val Lys Phe Leu His Asp Asn Lys Leu Thr His Thr
            275                 280                 285

Asp Leu Lys Pro Glu Asn Ile Leu Phe Val Asn Ser Asp Tyr Glu Leu
        290                 295                 300

Thr Tyr Asn Leu Glu Lys Lys Arg Asp Glu Arg Ser Val Lys Ser Thr
305                 310                 315                 320

Ala Val Arg Val Asp Phe Gly Ser Ala Thr Phe Asp His Glu His
                325                 330                 335

His Ser Thr Ile Val Ser Thr Arg His Tyr Arg Ala Pro Glu Val Ile
            340                 345                 350

Leu Glu Leu Gly Trp Ser Gln Pro Cys Asp Val Trp Ser Ile Gly Cys
            355                 360                 365

Ile Ile Phe Glu Tyr Tyr Val Gly Phe Thr Leu Phe Gln Thr His Asp
            370                 375                 380

Asn Arg Glu His Leu Ala Met Met Glu Arg Ile Leu Gly Pro Val Pro
385                 390                 395                 400

Ser Arg Met Ile Arg Lys Thr Arg Lys Gln Lys Tyr Phe Tyr Arg Gly
                405                 410                 415

Arg Leu Asp Trp Asp Glu Asn Thr Ser Ala Gly Arg Tyr Val Arg Glu
            420                 425                 430

Asn Cys Lys Pro Leu Arg Arg Tyr Leu Thr Ser Glu Ala Glu Asp His
            435                 440                 445

His Gln Leu Phe Asp Leu Ile Glu Asn Met Leu Glu Tyr Glu Pro Ala
        450                 455                 460

Lys Arg Leu Thr Leu Gly Glu Ala Leu Gln His Pro Phe Phe Ala Cys
465                 470                 475                 480

Leu Arg Thr Glu Pro Pro Asn Thr Lys Leu Trp Asp Ser Ser Arg Asp
                485                 490                 495

Ile Ser Arg
```

<210> SEQ ID NO 22
<211> LENGTH: 1538
<212> TYPE: DNA
<213> ORGANISM: Mus musculus

<400> SEQUENCE: 22

```
cgcacgggcc tcgccgccag aacgatgccc catccccgaa ggtaccattc ctcagagcga     60
ggtagccggg ggagttacca cgaacactat cagagccgaa agcataagcg aagaagaagt    120
cgctcctggt caagtagcag tgaccggaca aggcggcggc ggagggagga cagctaccac    180
gttcggtccc gaagcagcta tgatgaccat tcgtccgatc ggcggctgta cgatcggcgg    240
tactgtggca gctacaggcg caatgactac agccgggaca gaggggaggc ttactacgac    300
acagactttc ggcagtccta tgaataccat cgagagaaca gcagttaccg aagccagcgc    360
agcagccgaa ggaaacacag aaggcggagg agacggagcc ggacattcag ccgctcatct    420
tcacacagca gccggagagc caagagtgta gaggacgacg ctgagggcca cctcatctac    480
cacgtcgggg actggctaca agagcgatat gaaattgtaa gcaccttagg agaagggact    540
tcgggccgag ttgtgcagtg tgtggaccat cgcaggggcg aacacgagt tgccctgaag    600 atcattaaga atgtggagaa gtacaaggaa gcagcccgac tagaaatcaa cgtgctggag    660
aaaatcaatg agaaagatcc tgacaacaag aacctctgtg tccagatgtt tgactggttt    720
gactaccatg ccacatgtg tatctccttt gagcttctgg ccttagcac ttcgatttc    780 ctcaaagaca caaactacct gccctacccc atccaccaag tgcgccacat ggccttccag    840
```

```
ctctgccagg ccgtcaagtt cctccatgat aacaagttga cacatacgga cctcaaacct    900
gaaaatattc tgtttgtgaa ttcagactac gaactcacct acaacctaga agaagcga    960 gatgagcgca gtgtaaagag cacagccgtg cgggtggtgg acttcggcag tgccaccttt   1020
gaccacgaac accatagcac cattgtctcc actcgccatt accgagcccc cgaggtcatc   1080
ctggagttgg gctggtcaca gccatgcgat gtatggagca taggctgcat catctttgag   1140
tactacgttg gcttcaccct cttccagacc catgacaaca gagagcatct agccatgatg   1200
gaaaggatcc tgggtcctgt cccttctcgg atgatcagaa agacaagaaa acagaaatat   1260
ttttatcggg gtcgcctgga ttgggatgag aacacctcag ccggccgcta cgttcgtgag   1320
aactgcaaac ctctgcggcg gtatctgacc tcagaggcag aggaccacca ccagctcttc   1380
gatctgattg aaaatatgct agagtatgag cctgctaagc ggctgacctt aggtgaagcc   1440
cttcagcatc ctttcttcgc ctgccttcgg actgagccac ccaacaccaa gttgtgggac   1500
tccagtcggg atatcagtcg gtgacaatta ggctgggc                          1538
```

<210> SEQ ID NO 23
<211> LENGTH: 490
<212> TYPE: PRT
<213> ORGANISM: Mus musculus

<400> SEQUENCE: 23

```
Met His His Cys Lys Arg Tyr Arg Ser Pro Glu Pro Asp Pro Tyr Leu
 1               5                  10                  15

Thr Tyr Arg Trp Lys Arg Arg Ser Tyr Ser Arg Glu His Glu Gly
            20                  25                  30

Arg Leu Arg Tyr Pro Ser Arg Arg Glu Pro Pro Arg Arg Ser Arg
        35                  40                  45

Ser Arg Ser His Asp Arg Ile Pro Tyr Gln Arg Arg Tyr Arg Glu His
    50                  55                  60

Arg Asp Ser Asp Thr Tyr Arg Cys Glu Glu Arg Ser Pro Ser Phe Gly
65                  70                  75                  80

Glu Asp Cys Tyr Gly Ser Ser Arg Ser Arg His Arg Arg Ser Arg
                85                  90                  95

Glu Arg Ala Pro Tyr Arg Thr Arg Lys His Ala His Cys His Lys
            100                 105                 110

Arg Arg Thr Arg Ser Cys Ser Ser Ala Ser Ser Arg Ser Gln Gln Ser
        115                 120                 125

Ser Lys Arg Ser Ser Arg Ser Val Glu Asp Lys Glu Gly His Leu
    130                 135                 140

Val Cys Arg Ile Gly Asp Trp Leu Gln Glu Arg Tyr Glu Ile Val Gly
145                 150                 155                 160

Asn Leu Gly Glu Gly Thr Phe Gly Lys Val Val Glu Cys Leu Asp His
                165                 170                 175

Ala Arg Gly Lys Ser Gln Val Ala Leu Lys Ile Ile Arg Asn Val Gly
            180                 185                 190

Lys Tyr Arg Glu Ala Ala Arg Leu Glu Ile Asn Val Leu Lys Lys Ile
        195                 200                 205

Lys Glu Lys Asp Lys Glu Asn Lys Phe Leu Cys Val Leu Met Ser Asp
    210                 215                 220

Trp Phe Asn Phe His Gly His Met Cys Ile Ala Phe Glu Leu Leu Gly
225                 230                 235                 240

Lys Asn Thr Phe Glu Phe Leu Lys Glu Asn Asn Phe Gln Pro Tyr Pro
```

```
                245                  250                  255
Leu Pro His Val Arg His Met Ala Tyr Gln Leu Cys His Ala Leu Arg
            260                  265                  270

Phe Leu His Glu Asn Gln Leu Thr His Thr Asp Leu Lys Pro Glu Asn
        275                  280                  285

Ile Leu Phe Val Asn Ser Glu Phe Glu Thr Leu Tyr Asn Glu His Lys
    290                  295                  300

Ser Cys Glu Glu Lys Ser Val Lys Asn Thr Ser Ile Arg Val Ala Asp
305                  310                  315                  320

Phe Gly Ser Ala Thr Phe Asp His Glu His His Thr Thr Ile Val Ala
                325                  330                  335

Thr Arg His Tyr Arg Pro Pro Glu Val Ile Leu Glu Leu Gly Trp Ala
            340                  345                  350

Gln Pro Cys Asp Val Trp Ser Ile Gly Cys Ile Leu Phe Glu Tyr Tyr
        355                  360                  365

Arg Gly Phe Thr Leu Phe Gln Thr His Glu Asn Arg Glu His Leu Val
    370                  375                  380

Met Met Glu Lys Ile Leu Gly Pro Ile Pro Ser His Met Ile His Arg
385                  390                  395                  400

Thr Arg Lys Gln Lys Tyr Phe Tyr Lys Gly Gly Leu Val Trp Asp Glu
                405                  410                  415

Asn Ser Ser Asp Gly Arg Tyr Val Lys Glu Asn Cys Lys Pro Leu Lys
            420                  425                  430

Ser Tyr Met Leu Gln Asp Ser Leu Glu His Val Gln Leu Phe Asp Leu
        435                  440                  445

Met Arg Arg Met Leu Glu Phe Asp Pro Ala Gln Arg Ile Thr Leu Ala
    450                  455                  460

Glu Ala Leu Leu His Pro Phe Phe Ala Gly Leu Thr Pro Glu Glu Arg
465                  470                  475                  480

Ser Phe His Ser Ser Arg Asn Pro Ser Arg
                485                  490

<210> SEQ ID NO 24
<211> LENGTH: 1787
<212> TYPE: DNA
<213> ORGANISM: Mus musculus

<400> SEQUENCE: 24
ctgcaggtcg acactagtgg atccaaagaa ttcggcacga cgcagccgg agcctgggag      60 acgatgcatc actgtaagcg ataccgttcc ccagagccag acccataccgt gacgtaccgc    120 tggaagagga ggcggtctta cagtcgggag catgaaggtc gactacgata cccatcccga    180
agggagcctc ccccacggag atcacggtcc agaagccatg atcgtatacc ctaccagcgg    240
aggtaccggg aacaccgtga cagtgatacg tatcggtgtg aagagcggag ccatcttttt    300
ggagaggact gctatgggtc ttcacgttct gcacatcgga gacggtcacg agagagggcg    360
ccgtaccgta cccgcaagca tgcccaccac tgtcacaaac gccgtaccag gtcttgtagc    420
agtgcttcct cgagaagcca acagagcagt aagcgcagca gccggagtgt ggaagatgac    480
aaggagggcc acctggtgtg ccggatcggc gattggctcc aagagcgata tgagatcgtg    540
gggaacctgg gtgaaggcac ctttggcaag gtggtggagt gcttggacca tgccagaggg    600
aagtcacagg ttgccctgaa gatcatccgt aatgtgggca agtatcggga agctgctcgt    660
ctagaaatta tgttctcaa gaaaatcaag gagaaagaca aggaaaataa gttcctttgt    720
```

```
gtcctgatgt ctgactggtt caacttccat ggtcatatgt gcatcgcctt tgagctcctg    780
ggcaagaaca cctttgagtt cctgaaggag aacaacttcc agccttaccc cctaccacat    840
gtccggcaca tggcctacca gctctgtcat gcccttagat ttctacacga gaaccagctg    900
acccacacag acttgaagcc agagaacatc ttgtttgtga attctgagtt tgaaaccctc    960
tacaatgagc acaagagctg cgaggagaag tcagtgaaga acaccagcat ccgagtggca   1020
gactttggca gtgccacgtt tgaccatgaa catcacacca ccattgtggc cacccgtcac   1080
taccgcccac ctgaggtgat ccttgagctg ggctgggcac agccttgtga tgtctggagt   1140
atcggctgca ttctctttga gtactaccgt ggctttacac tcttccagac ccatgaaaat   1200
agagaacact tggttatgat ggagaagatt ctaggaccca tcccatcaca catgatccac   1260
cgtaccagga agcagaaata tttctacaaa gggggcctgg tttgggatga aacagctct    1320
gatgggcggt atgtgaagga aactgcaaa cctctgaaga gttacatgct gcaggactcc    1380
ctggagcatg tgcagctgtt tgacctgatg aggaggatgt tagagttcga ccctgctcag   1440
cgcatcacat tggcagaagc cttgctgcac cccttctttg ctggcctgac ccctgaggag   1500
cggtccttcc acagcagccg taaccccagc agatgacagg tgcaggccag cacacgaaga   1560
gttggagagc tggactgggc tgctggcccc ttttctccag cctctcccac tggcctcaga   1620
gccagagcca ccgatgaaca gtgcaatgtg aaggaaggca ggacctgcaa gggaaggggg   1680
aatgtggtgc ccggctgcca gaaagcacag attggaccca agctttttata tgttgtaaag   1740
ttataataaa gtgttcttac tgtttgtaaa aaaaaaaaa aaaaaaa                  1787
```

```
<210> SEQ ID NO 25
<211> LENGTH: 481
<212> TYPE: PRT
<213> ORGANISM: Mus musculus

<400> SEQUENCE: 25

Met Arg His Ser Lys Arg Thr His Cys Pro Asp Trp Asp Ser Arg Glu
1               5                   10                  15

Ser Trp Gly His Glu Ser Tyr Ser Gly Ser His Lys Arg Lys Arg Arg
            20                  25                  30

Ser His Ser Ser Thr Gln Glu Asn Arg His Cys Lys Pro His His Gln
        35                  40                  45

Phe Lys Asp Ser Asp Cys His Tyr Leu Glu Ala Arg Cys Leu Asn Glu
    50                  55                  60

Arg Asp Tyr Arg Asp Arg Tyr Ile Asp Glu Tyr Arg Asn Asp Tyr
65                  70                  75                  80

Cys Glu Gly Tyr Val Pro Arg His Tyr His Arg Asp Val Glu Ser Thr
                85                  90                  95

Tyr Arg Ile His Cys Ser Lys Ser Ser Val Arg Ser Arg Ser Ser
            100                 105                 110

Pro Lys Arg Lys Arg Asn Arg Pro Cys Ala Ser His Gln Ser His Ser
        115                 120                 125

Lys Ser His Arg Arg Lys Arg Ser Arg Ser Ile Glu Asp Asp Glu Glu
    130                 135                 140

Gly His Leu Ile Cys Gln Ser Gly Asp Val Leu Arg Ala Arg Tyr Glu
145                 150                 155                 160

Ile Val Asp Thr Leu Gly Glu Gly Ala Phe Gly Lys Val Val Glu Cys
                165                 170                 175

Ile Asp His Gly Met Asp Gly Leu His Val Ala Val Lys Ile Val Lys
            180                 185                 190
```

```
Asn Val Gly Arg Tyr Arg Glu Ala Ala Arg Ser Glu Ile Gln Val Leu
        195                 200                 205

Glu His Leu Asn Ser Thr Asp Pro Asn Ser Val Phe Arg Cys Val Gln
        210                 215                 220

Met Leu Glu Trp Phe Asp His Gly His Val Cys Ile Val Phe Glu
225                 230                 235                 240

Leu Leu Gly Leu Ser Thr Tyr Asp Phe Ile Lys Glu Asn Ser Phe Leu
                245                 250                 255

Pro Phe Gln Ile Asp His Ile Arg Gln Met Ala Tyr Gln Ile Cys Gln
                260                 265                 270

Ser Ile Asn Phe Leu His His Asn Lys Leu Thr His Thr Asp Leu Lys
                275                 280                 285

Pro Glu Asn Ile Leu Phe Val Lys Ser Asp Tyr Val Val Lys Tyr Asn
        290                 295                 300

Ser Lys Met Lys Arg Asp Glu Arg Thr Leu Lys Asn Thr Asp Ile Lys
305                 310                 315                 320

Val Val Asp Phe Gly Ser Ala Thr Tyr Asp Asp Glu His His Ser Thr
                325                 330                 335

Leu Val Ser Thr Arg His Tyr Arg Ala Pro Glu Val Ile Leu Ala Leu
                340                 345                 350

Gly Trp Ser Gln Pro Cys Asp Val Trp Ser Ile Gly Cys Ile Leu Ile
                355                 360                 365

Glu Tyr Tyr Leu Gly Phe Thr Val Phe Gln Thr His Asp Ser Lys Glu
        370                 375                 380

His Leu Ala Met Met Glu Arg Ile Leu Gly Pro Ile Pro Ala His Met
385                 390                 395                 400

Ile Gln Lys Thr Arg Lys Arg Lys Tyr Phe His His Asn Gln Leu Asp
                405                 410                 415

Trp Asp Glu His Ser Ser Ala Gly Arg Tyr Val Arg Arg Arg Cys Lys
                420                 425                 430

Pro Leu Lys Glu Phe Met Leu Cys His Asp Glu Glu His Glu Lys Leu
        435                 440                 445

Phe Asp Leu Val Arg Arg Met Leu Glu Tyr Asp Pro Ala Arg Arg Ile
450                 455                 460

Thr Leu Asp Glu Ala Leu Gln His Pro Phe Phe Asp Leu Leu Lys Arg
465                 470                 475                 480

Lys

<210> SEQ ID NO 26
<211> LENGTH: 1549
<212> TYPE: DNA
<213> ORGANISM: Mus musculus

<400> SEQUENCE: 26
aaagagacgc agcggctgga gaggaacgac ggcggtttgg cgacatttct gcccaaaagg        60
ccgcttgctt ttgcggagat gcggcattcc aaacgaactc actgtcctga ttgggatagt       120
agagaaagct ggggccatga agctacagt ggaagtcaca aacgcaagag aaggtctcac        180
agcagtactc aggagaacag gcactgtaaa ccacatcatc agtttaaaga ctcggattgt       240
cactatttag aagcaagatg cttgaatgag agagattatc gggaccggag atacattgat       300
gaatacagaa atgactactg cgaaggatat gttccaagac attaccatag agacgttgaa       360
agcacttacc ggatccattg cagtaaatcc tcagtcagga gcaggagaag cagccctaag       420
```

-continued

```
agaaagcgta atagaccctg tgcaagtcat cagtcgcatt cgaagagcca ccgaaggaaa    480
agatccagga gtatagagga tgatgaggag ggtcacctga tctgtcaaag tggagacgtt    540
ctaagagcaa gatatgaaat cgtggacact ttaggtgaag gagcctttgg caaagttgta    600
gagtgcattg atcacggcat ggatggctta catgtagcag tgaaaattgt aaaaaatgta    660
ggacgttacc gggaggcagc tcgttctgaa atccaagtat tggagcactt gaacagcact    720
gaccccaaca gtgtcttccg atgcgtccag atgctagagt ggtttgatca tcatggtcat    780
gtttgtattg tgtttgagct gctgggactt agtacctatg attttattaa agaaaatagt    840
tttctgccat ttcaaattga tcacatcagg caaatggctt atcagatctg ccagtctata    900 aatttttttac atcataataa attaacacac acggacctaa aacctgaaaa tattttattt    960
gtgaagtctg actatgtagt caaatacaat tctaaaatga aacgagatga gcgcacattg   1020
aaaaacacag atatcaaagt tgttgatttt ggaagtgcaa catatgacga cgaacatcat   1080
agtactttgg tgtccacaag gcactacagg gctccagagg tcattttggc tctaggttgg   1140
tctcagcctt gtgatgtttg gagcataggc tgcattctta ttgagtacta ccttgggttc   1200
acagtctttc agaccacga tagtaaagag cacctggcaa tgatggagcg gatcttagga   1260
cccatcccag cacatatgat ccagaagaca aggaaacgca agtatttcca ccataaccag   1320
ctagattggg acgagcatag ttcagctggg agatatgtta ggagacgctg caagccgtta   1380
aaggaattta tgctgtgtca tgacgaagag catgagaagc tgtttgacct ggttcgaaga   1440
atgttggagt atgacccagc gagaaggatc accttggatg aagcattgca gcacctttc    1500 tttgacttat taaaaggaa atgagtggga gtcagggcgg ccgcaccgc              1549
```